(12) United States Patent
Shen et al.

(10) Patent No.: US 6,787,165 B2
(45) Date of Patent: Sep. 7, 2004

(54) COMPOSITION COMPRISING EXTRACTS OF FLOS LONICERAE, FRUCTUS FORSYTHIAE AND RADIX SCUTELLARIAE, USES AND PREPARATION THEREOF

(75) Inventors: Ping Niang Shen, Shanghai (CN); Ke Feng Ruan, Shanghai (CN); Yu Lan Wang, Shanghai (CN); Wei Yu, Shanghai (CN); Wen Qing Zhang, Shanghai (CN); Xiao Kun Hong, Shanghai (CN); Xin Hong Wang, Shanghai (CN)

(73) Assignee: National Engineering Research Center for Traditional Chinese Medicine, Shanghai (CN)

( * ) Notice: Subject to any disclaimer, the term of this patent is extended or adjusted under 35 U.S.C. 154(b) by 0 days.

(21) Appl. No.: 10/032,514

(22) Filed: Oct. 24, 2001

(65) Prior Publication Data
US 2002/0168426 A1 Nov. 14, 2002

(30) Foreign Application Priority Data
Oct. 25, 2000 (CN) ........................................ 00125764 A

(51) Int. Cl.[7] ............................................. A01N 65/00
(52) U.S. Cl. ....................... 424/741; 424/404; 424/777; 424/778
(58) Field of Search ................................ 424/741, 777, 424/778, 404, 773, 9.2; 436/8

(56) References Cited

U.S. PATENT DOCUMENTS

| 5,443,839 A | 8/1995 | Meybeck |
| 5,834,000 A | 11/1998 | Yng-Wong |
| 5,908,628 A | 6/1999 | Hou et al. |
| 5,989,556 A | 11/1999 | Tsai et al. |
| 6,083,921 A | 7/2000 | Xu |

FOREIGN PATENT DOCUMENTS

| JP | 63239228 | 10/1988 |
| JP | 02264663 | 10/1990 |
| JP | 05194246 | 8/1993 |
| JP | 0928673 | 11/1997 |
| WO | 348509 | 1/1990 |
| WO | 598001 | 3/1993 |
| WO | PCT/CN97/00001 | 8/1997 |
| WO | WO 99/34812 | * 7/1999 |
| WO | PCT/US01/50424 | 9/2003 |

OTHER PUBLICATIONS

Houghton et al., Phytotherapy Research (1993), 7: 384–386. A Clinical Evaluation of the Chinese Herbal Mixture 'Aden–1' for Treating Respiratory Infections.*
Matsuse et al., Journal of Traditional Medicines (1998), 15: 52–56, Effect of Shuang Huang Lian on hepatitis B virus surface antigen secretion.*
Luan S et al., Journal of Chinese Materia Medica (1991), 16(10): 602–3. Signal multiplier spectrophotometric determination of baicalin, chlorogenic acid and phillyrin in shuang huanglian injection. Abstract.*
Moyler, David A., Extraction of Essential Oils with Carbon Dioxide, Flavor and Fragrance Journal, vol. 8, 235–147 (1993), 235–247.
PCT Notification of Transmittal of International Preliminary Examination Report, issued on Jan. 2, 2004, for International application No. PCT/US01/50424, filed on Oct. 24, 2001 [Exhibit 1].

* cited by examiner

Primary Examiner—Christopher R. Tate
Assistant Examiner—Michele C. Flood
(74) Attorney, Agent, or Firm—Albert Wai-Kit Chan; Mark Elkins

(57) ABSTRACT

The invention provides a new formulation of the composition comprising Flos Lonicerae Fructus Forsythiae and Radix Scutellariae. This invention also provides a method for identification with HPLC and the characteristic peaks of the compositions of said composition. The composition possesses antiviral effective, namely, inhibition of influenza virus, parainfluenza virus, herpes I virus and herpes II virus. The invention refers to a method for preparation and control of the active components of Flos Lonicerae Fructus Forsythiae and Radix Scutellariae for its biological activity. The invention also provides a unique raw materials and intermediate formulation.

12 Claims, 7 Drawing Sheets

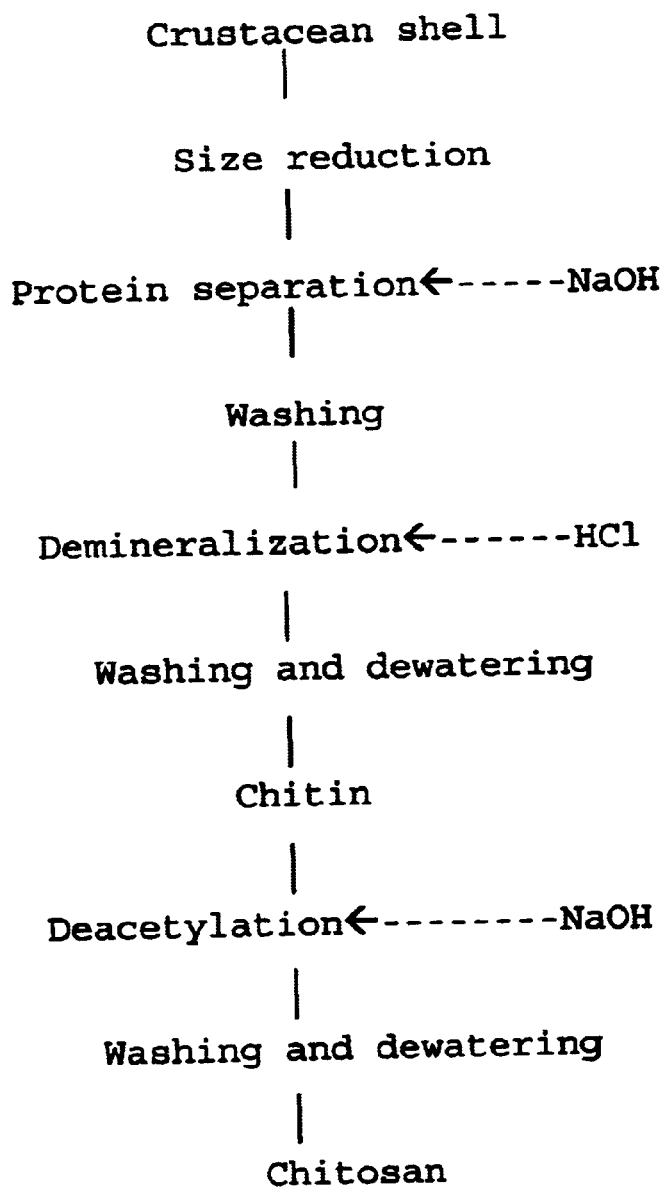
Figure 1. Flow chart for Chitosan preparation

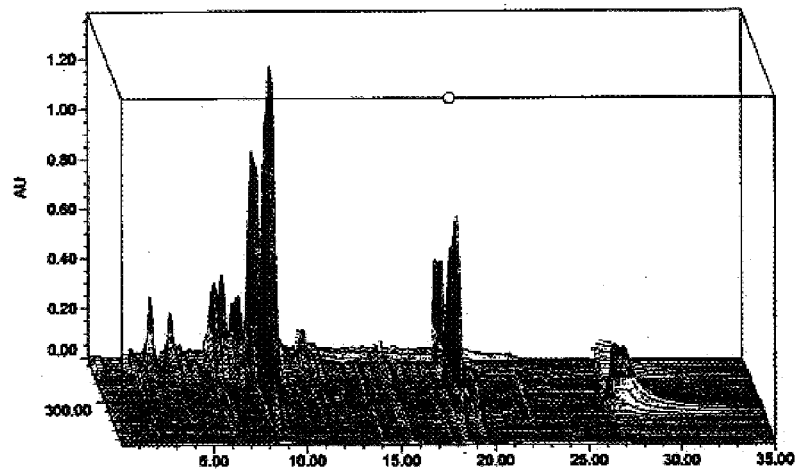
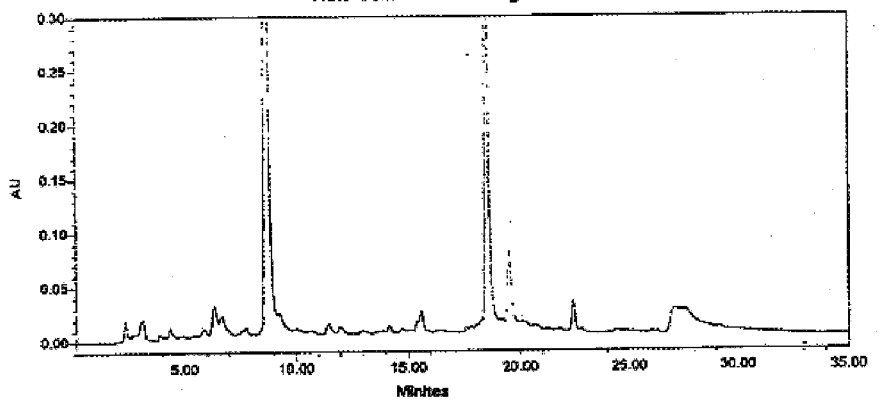

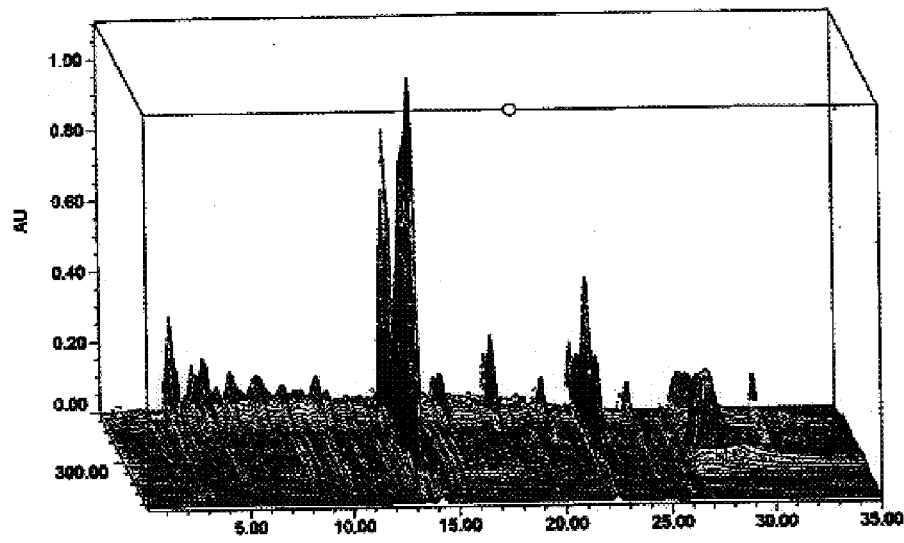
FIGURE 3. 3D-Spectro-Chromatogram of Fructus Forsythiae
Sample Information
| | | | |
|---|---|---|---|
| SampleName | lian yaocai | Sample Type | Unknown |
| Vial | 1 | Date Acquired | 12/19/2000 3:49:07 PM |
| Injection | 1 | Acq Method Set | zou |
| Injection Volume | 5.00 ul | Processing Method | a |
| Channel | 996 | Date Processed | 7/6/2001 5:27:43 PM |
| Run Time | 35.0 Minutes | | |
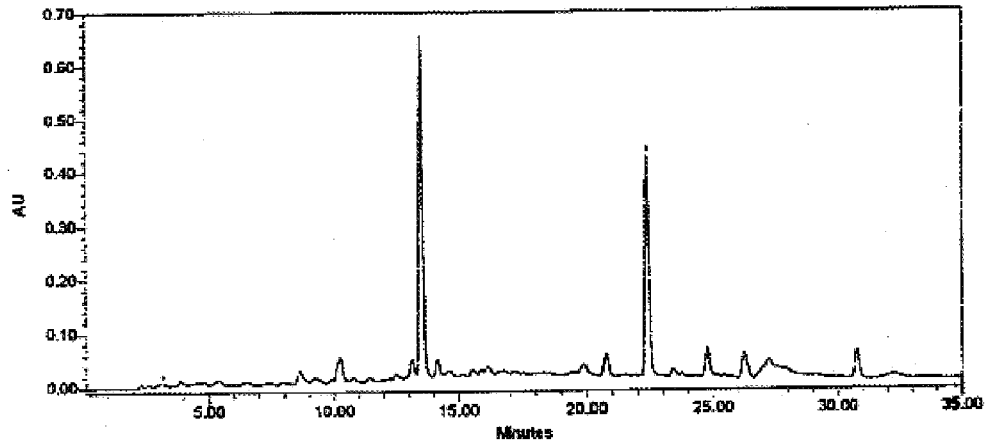

FIGURE 4. 3D-Spectro-Chromatogram of Radix Scutellariae
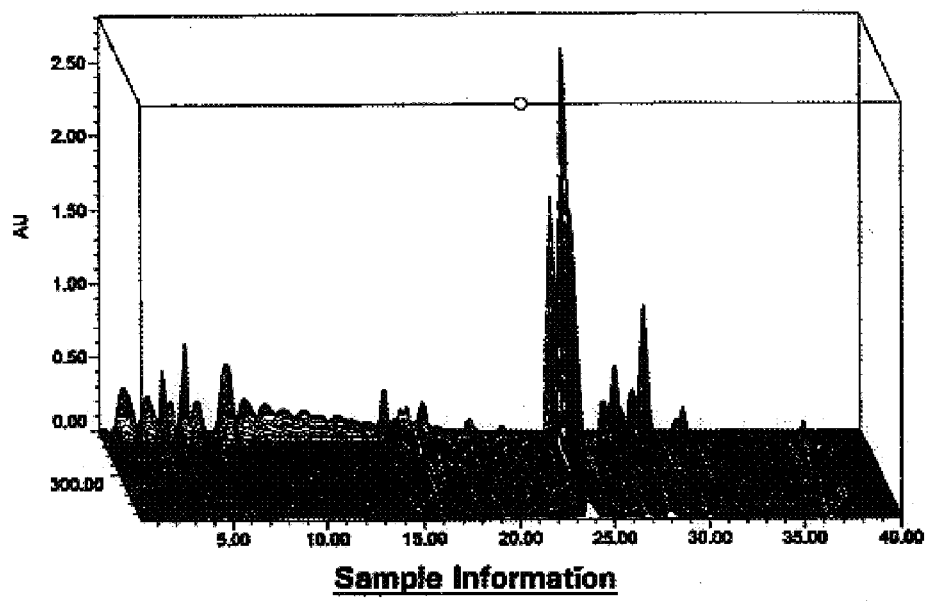
Sample Information
| | | | |
|---|---|---|---|
| SampleName | huanqinyaocai | Sample Type | Unknown |
| Vial | 1 | Date Acquired | 4/6/2000 4:25:38 PM |
| Injection | 2 | Acq Method Set | zou |
| Injection Volume | 20.00 ul | Processing Method | e |
| Channel | 996 | Date Processed | 7/6/2001 5:41:20 PM |
| Run Time | 40.0 Minutes | | |
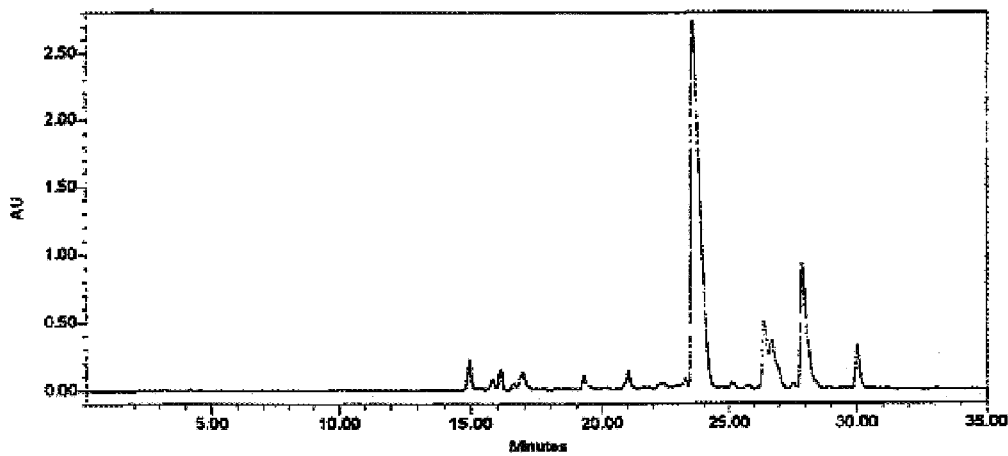

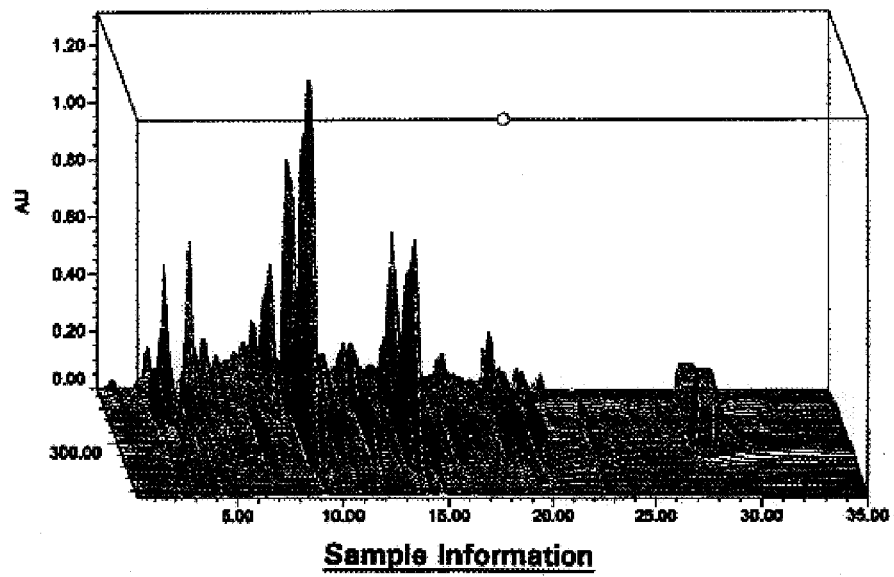
FIGURE 5. 3D-Spectro-Chromatogram of extract of Flos Lonicerae and Fructus Forsythiae
Sample Information
| | | | |
|---|---|---|---|
| SampleName | jin+lian tiquwu | Sample Type | Unknown |
| Vial | 1 | Date Acquired | 12/19/2000 11:48:37 PM |
| Injection | 1 | Acq Method Set | zou |
| Injection Volume | 20.00 ul | Processing Method | a |
| Channel | 996 | Date Processed | 7/6/2001 4:58:57 PM |
| Run Time | 35.0 Minutes | | |
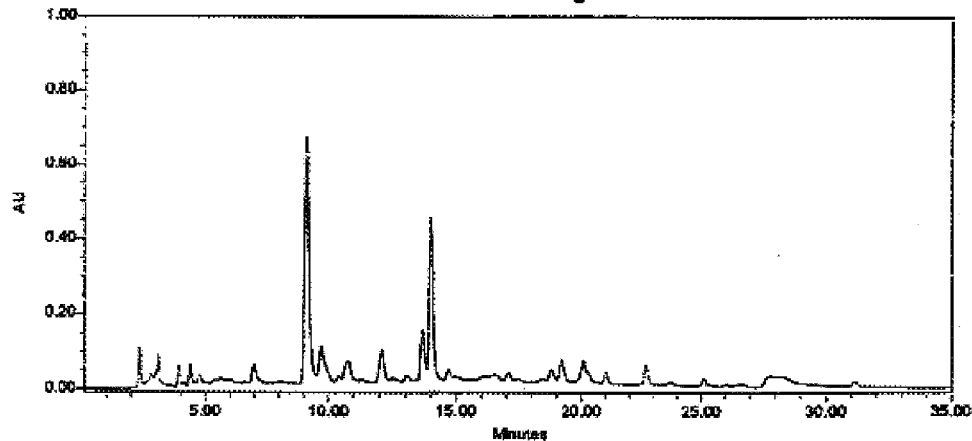

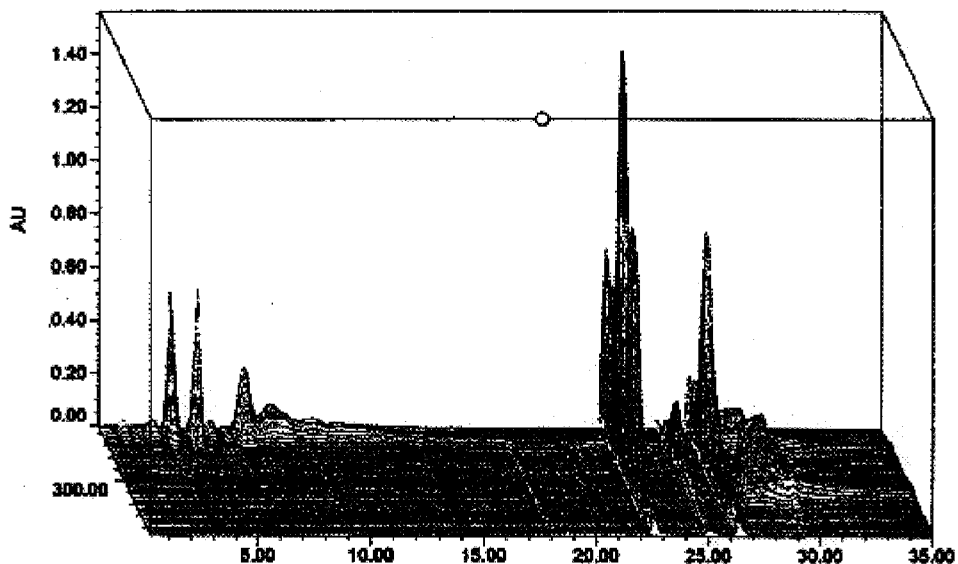
FIGURE 6. 3D-Spectro-Chromatogram of the extract of Radix Scutellariae
Sample Information
| | | | |
|---|---|---|---|
| SampleName | huanqincupin | Sample Type | Unknown |
| Vial | 1 | Date Acquired | 12/19/2000 12:52:39 PM |
| Injection | 1 | Acq Method Set | zou |
| Injection Volume | 20.00 ul | Processing Method | e |
| Channel | 996 | Date Processed | 7/6/2001 4:50:07 PM |
| Run Time | 35.0 Minutes | | |
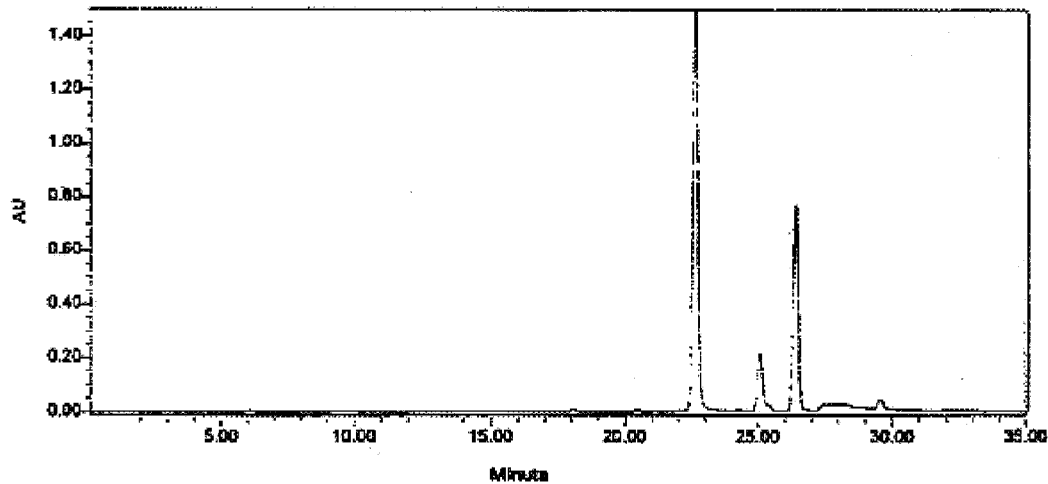

FIGURE 7. 3D-Spectro-Chromatogram of drug product of Flos Lonicerae, Fructus Forsythiae and Radix Scutellariae
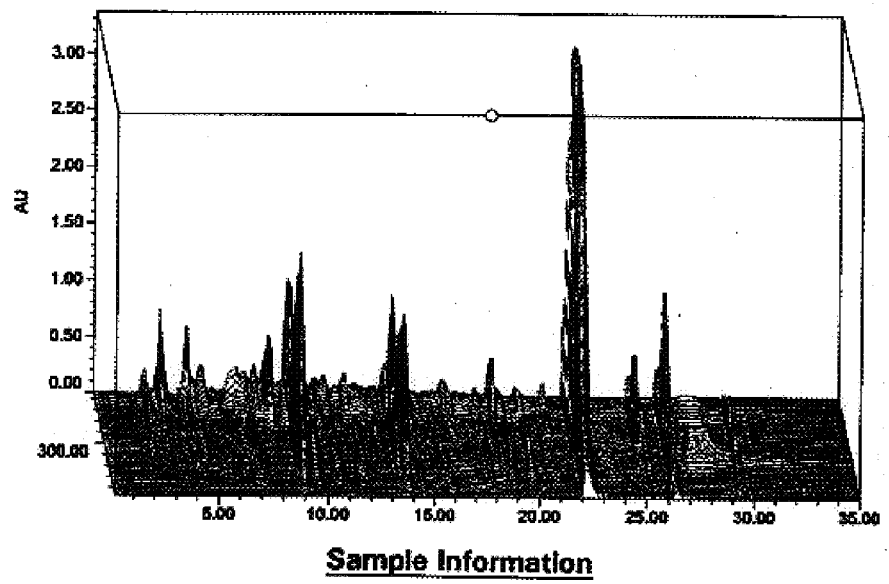
Sample Information
| | | | |
|---|---|---|---|
| SampleName | suanhuanlian | Sample Type | Unknown |
| Vial | 1 | Date Acquired | 12/19/2000 1:55:34 PM |
| Injection | 1 | Acq Method Set | zou |
| Injection Volume | 20.00 ul | Processing Method | a |
| Channel | 996 | Date Processed | 12/19/2000 3:40:06 PM |
| Run Time | 35.0 Minutes | | |
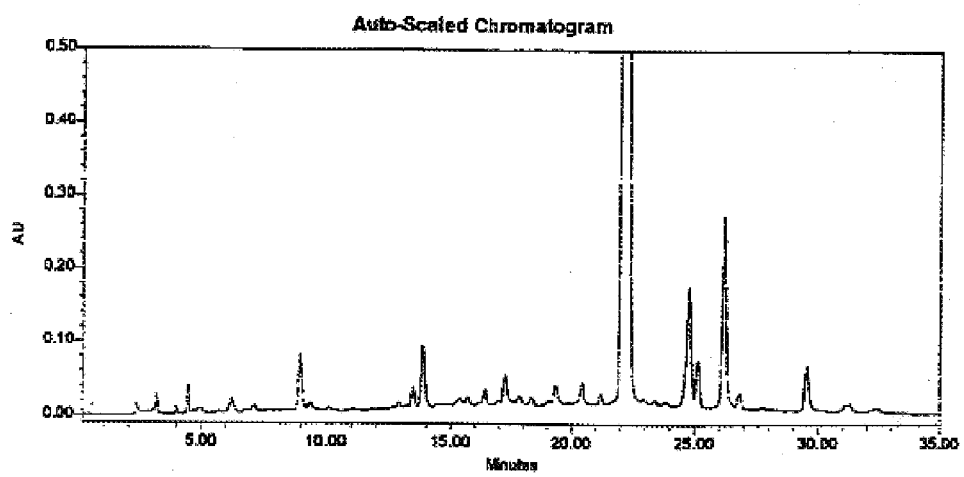

COMPOSITION COMPRISING EXTRACTS OF FLOS LONICERAE, FRUCTUS FORSYTHIAE AND RADIX SCUTELLARIAE, USES AND PREPARATION THEREOF

Throughout this application, various publications are referenced to and the disclosures of these publications are hereby incorporated by reference into this application in order to more fully describe the state of the art as known to the skilled therein as of this date of the invention described and claimed herein.

BACKGROUND OF THE INVENTION

This invention relates to a composition comprising extracts of flos lonicerae, fructus forsythiae and radix scutellariae, uses and preparation thereof. This composition could be used for the inhibition of influenza virus, parainfluenza virus, herpes I virus and herpes II virus.

Influenza is the most frequent cause of acute respiratory illness that could require medical intervention. It affects all age groups and it can recur to any individual. A study involving some residents of a nursing home that suffer from respiratory viral diseases was conducted between 1988 and 1999. The results showed a thirty-day mortality of 4.7% (15/322) for influenza A, 5.4% (7/129) for influenza B, 6.1% (3/49) for parainfluenza type I, 0% (0/26) for parainfluenza type II, type III and type IV, 0% (0/26) for respiratory syncytial virus (RSV), and 1.6% (1/61) for rhinovirus. The herpes simplex virus infection is an important risk factor caused cervical carcinoma, AIDS, Alzheimer's disease. The rates of herpes simplex virus (HSV) infection are rising, the highest prevalence being in the group infected with the Human Immunodeficiency Virus (HIV).

During the past three decades, efforts to prevent and control influenza have focused primarily on the use of inactivated influenza vaccines in elderly people and in individuals with chronic medical conditions. However, the continuing impact of influenza in these and other population groups has motivated the development of novel approaches for prevention and control of influenza. Several important advances in the field of influenza have occurred in the last few years. New antiviral drugs based on the structure of the neuraminidase molecule were assessed in clinical trials and found to be effective against influenza A and B viruses. In recent year, the research and development of nature products for influenza virus and herpes simplex virus are gradually increasing in importance. Studies from Dr. Mori K, Kampo Pharmacology Department, Central Research Laboratories, Tsumara of Japan showed that the Hochu-ekki-to (TJ-41), a Japanese herbal medicine was found to increase the survival rate of mice, prolong the mean survival days, and suppress viral growth in bronchoalveolar labage fluid (BALF). This medicine inhibited the lung index (lung consolidation) four days after the mice were infected with influenza. The agent had been administered 7 days before injection of the virus and 4 days after injection. The results suggested that the TJ-41 exerts its inhibitory effects over the influenza virus infection via enhancement of the host immune responses in this experimental murine system. Dr. Mantani N, Department of Japanese Oriental Medicine, Toyama Medical and Pharmaceutical University, conducted a vital fluorescence microscopic study. It showed that the extract of Ephedrae herba (EHext) inhibited acidification of endosomes and lysosomes in a concentration-dependent manner (100–400 mg/ml). Moreover the growth of influenza A/PR/8/34 (H1N1) (PR8) virus was inhibited when the cells were treated with EHext for one hour immediately after infection, or treated as early as 5–10 min after the infection.

Gingyo-san is a natural product containing extracts from seven medicinal plants and fermented soybeans in a specific ratio. It has been used as a therapeutic agent for the common cold in China. Dr. Kurokawa M, Department of Virology, Toyama Medical and Pharmaceutical University of Japan, found that two components extracted from Glycyrrhizae radix and Arctii Fructus presented anti-influenza viral activities in mice infected with influenza A2 virus. Dr. Yamada H, Oriental Medicine Research Center, Kitasato Institute of Japan studied the anti-virus activity of Sho-seiryu-to (SST). He suggested that SST was useful for influenza virus infection on aged people and for cross-protection of subtypes of influenza A viruses and influenza B virus, and was also useful for the treatment of patients who had a history of influenza virus infection and/or influenza vaccination. Dr. Hayashi K, Department of Virology, Toyama Medical and Pharmaceutical University studied the activities of thirteen sesquiterpenes isolated from *Tripterygium wilfordii* Hook fil. var. *regelii* Makino against herpes simplex virus type 1 (HSV-1) in vitro. He found that the triptofordin C-2 suppressed viral protein synthesis of infected cells when added at the early steps of the HSV-1 replication and exerted inhibition of translation of the transcripts of the immediate early genes. Radix bupleuri, a Chinese medicinal herb used for the treatment of influenza, malaria and menstrual disorders, was extracted with hot water and separated into five different fractions (RB, RBI, RBII, RBIII and RBIV) by stepwise alcohol precipitation. Dr. Kok LD, Department of Biochemistry, Chinese University of Hong Kong, found that RBIII exhibited a potent activating effect on the cytotoxic activity of macrophages, NK and LAK cells against tumor cells in his studies. Dr. Ball MA investigated the antiviral effect of the Keishi-ni-eppi-ichi-to (TJS-064) in mice infected with the influenza A2 (H2N2) virus. The result showed that pulmonary consolidations, virus titers in lung tissues and HAI titers in sera of infected mice treated with TJS-064 were all significantly lower compare with those of infected mice treated with saline. Dr. Fu HY presented the decoction of Gui Zhi Tang (DGZT), which had the action of bidirectional regulation and normalization in polyhidrosis induced by aminopyrine or in the case of hypohidrosis induced by ropineonrats.

The product obtained from this invention is an effective agent for inhibition of influenza virus, parainfluenza virus, herpes I virus and herpes II virus. The composition of this Chinese herbal medicine comprises three herbal components: Radix Scutellariae, Fructus Forsythiae and Flos Lonicerae. The pharmacological characteristics and efficacy relating to the compositions had been confirmed in previous studies.

Wang Y H, the Second Hospital of Harbin Medical University, presented a result of clinical research in his publication. Two hundred and two cases of acute respiratory tract infection (ARI) were treated with Shuanghuanglian (SHL) aerosol, an antiviral agent. Among them, 64% of the cases were caused from Respiratory Syncytial Virus (RSV). The virostatic and bacteriostatic tests were done in vitro by the cell culture method. The results showed that SHL could inhibit the RSV, parainfluenza I-IV and 23 kinds of pathogenic bacteria such as the *Staphylococcus aureus*. The bacteriostatic effect was positively correlated to the SHL concentration. Experimental studies showed that SHL could enhance the NK cell activity, promote the production of alpha-interferon and raise the rate of lymphocyte transformation. The controlled observation on SHL preparation with various dosage-forms revealed that the SHL aerosol was effective in treating early ARI. This drug showed better results when compare to the results from the injections and oral liquor symptom etiologically (P<0.01). Its effective rate was 96%.

Some studies were conducted with herbal products for anti-inflammation or/and anti-virus, which include herbal components comprising Radix Scutellariae or Fructus Forsythiae or Flos Lonicerae. However, there were differences of the formula, content and efficiency of effective composition compared with the invention.

U.S. Pat. No. 5,908,628 refers to a therapeutic composition for the treatment of pain, fever and inflammation, which includes some herbal components, one of them is Fructus Forsythiae. The percentage of Fructus Forsythiae is only 5–15% and the range of weight is 170–190 g in the composition.

In U.S. Pat. No. 5,834,000, a pharmacologically effective composition was studied. The composition, comprising *Isatides tinctoria*, Forsythia fructus, Lonicera flos et al, showed antiviral and antimicrobial activities. The weight percent of *Isatides tinctoria* is about 37.5%, and 5% of Forsythia fructus and Lonicera flos. Forsythia fructus and Lonicera flos can relieve sore throat symptoms and reduce fever without unwanted side effects. There is a difference in the percentage and composition of effective ingredients when compared with this invention of which the percentage of Forsythia fructus is about 50% and for the Lonicera flos is 25%.

U.S. Pat. No. 5,989,556 pertains to the compositions derived from Chinese herbal medicines, medicinal plants and extracts thereof, which are used for treatment of infected animals, especially those with hepatitis B and C viruses (HBV & HCV), and Human Immunodeficiency Virus (HIV). The compositions contain forsythiae fructus, lonicerae flos or scutellariae in various groups.

The SHL agent is extracted with ancient techniques that have been used in traditional Chinese medicine for a long period of time. In the early 70's, the SHL was used to treat upper respiratory tract infection. The statistics from Pediatrics Department of Haerbin Medical University of China indicated that the effective rate of pediatric pneumonia was about 92.5% and the cure rate was around 80.8%. In the early 90's, the Ministry of Public Health of China approved different kinds of devices for the use of SHL such as powder injection, water injection, oral liquid, aerosol and tablet. But none of these devices were very effective in the way they were produced and administered.

This invention is the second development of the SHL tablet. The technique of preparation, composition and efficacy for the treatment of inhibition of influenza virus, parainfluenza virus, herpes I virus and herpes II virus were further improved in this invention.

This invention refers to an herbal composition that inhibits the influenza virus, parainfluenza virus, herpes I virus and herpes II virus. This invention derives from an herbal composition. Wherein said composition comprises Flos Lonicerae, Fructus Forsythiae, Radix Scutellariae. This invention includes a method for identification with HPLC and the characteristic peaks of the compositions of the raw materials, drug substances and drug product. The invention refers to a special extraction, wherein said extraction comprises CO2 supercritical fluid extraction consisting of Flos Lonicerae and Fructus Forsythiae, subboiling aqueous extraction, flocculation and alcohol precipitation. The invention refers to a unique intermediate formulae, wherein said formulae comprises about 90–180 g of drug substance of 10–60 g of Flos Lonicerae and Fructus Forsythiae, 10–60 g of supercritical extracta of Flos Lonicerae and Fructus Forsythiae and about 30–50 g of Radix Scutellariae extract. This current preparation was made more effective than the one used in previous techniques.

BRIEF DESCRIPTION OF THE DRAWINGS

FIG. 1 shows the process of Chitosan preparation.

FIG. 2 shows the 3D-Spectro-Chromatogram of Flos Lonicerae raw material, wherein the numbers of peaks are about 8 through 11. The $4^{th}$ peak is a certified characteristic/comparable peak of Chlorogenic acid.

FIG. 3 shows the 3D-Spectro-Chromatogram of Fructus Forsythiae raw material, wherein the numbers of peaks are about 11 through 14. The $8^{th}$ peak is a certified characteristic/comparable peak of Phillyrin.

FIG. 4 shows the 3D-Spectro-Chromatogram of Radix Scutellariae raw material, wherein the numbers of peaks are about 22 through 25. The $12^{th}$ peak is a certified characteristic/comparable peak of Baicalin and the $21^{st}$ peak is a certified characteristic/comparable peak of Baicalein.

FIG. 5 shows the 3D-Spectro-Chromatogram of the extracts of Flos Lonicerae and Fructus Forsythiae, wherein the numbers of peaks are about 18 through 21. The $8^{th}$, the $10^{th}$ and the $16^{th}$ peaks sequentially is the certified characteristic peaks of Chlorogenic acid, Caffeic acid and Phillyrin.

FIG. 6 shows the 3D-Spectro-Chromatogram of Radix Scutellariae extract, wherein the numbers of peaks are about 4 through 5. The $1^{st}$ peak is a certified characteristic peak of Baicalin. The $5^{th}$ peak is a certified characteristic peak of Baicalein.

FIG. 7 shows the 3D-Spectro-Chromatogram of the drug product comprising Flos Lonicerae, Fructus Forsythiae, Radix Scutellariae, wherein the numbers of peaks are about 27 through 30. The $8^{th}$, the $12^{th}$, the $20^{th}$, the $22^{nd}$ and the $28^{th}$ peaks is respectively the certified characteristic peaks of Chlorogenic acid, Caffeic acid, Phillyrin, Baicalin and Baicalein.

DETAILED DESCRIPTION OF THE INVENTION

This invention provides a composition comprising effective amount of extracts from Flos Lonicerae Fructus Forsythiae and Radix Scutellariae. This invention also provides an antiviral and antibacterial pharmaceutical composition comprising effective amount of Flos Lonicerae Fructus Forsythiae and Radix Scutellariae. This invention provides the above compositions, wherein the ratio of is 1:2:1. The ratio of the plants are adjustable and could have similar efficacious effect in treating different diseases.

This invention also provides a method for identifying the composition of Flos Lonicerae raw material, which comprises the steps of: a) using Chlorogenic acid as the standard and using Flos Lonicerae raw material as a sample; b) preparing the sample solution of Flos Lonicerar raw material further comprising the steps of: i) Taking some Flos Lonicerae, rub it into powder and then pass the 40 item of bolt; ii) weighing exactly 187.5 mg and put it into the centrifuge tube; adding 4 ml of methanol/water to a volute mixer and mix for 1 min. Then ultrasonically vibrate and extract for 15 min, centrifuge it, and take the upper solution; iii) adding 4 ml of methanol/water and ultrasonically vibrate and extract the residue for another 15 min. Centrifuge and take the upper clear solution; iv) Washing the residue with 1.5 ml of methanol/water and combine it with the upper clear solution. Scale the sample solution in a 10 ml of flask. v) filtering it with 0.45 μm filtration membrane before giving sample; c) performing he Fingerprint Chromatogram (HPLC-FPS) of Flos Lonicerae raw material under the following conditions:

| Conditions of Raw Material HPLC-FPS | | | | | | |
|---|---|---|---|---|---|---|
| Chromatographic Column | Protecting Column | Floating Phase | Temperature | Inspector | Injection Volum | Run Time (min) |
| Inertial ODS-3, 5 μm 4.6 mm*250 mm | phenomene x C18(ODS), 4 mm*3 mm ID | 1% acetic acid solution | room temperature | PDA210~400 nm of wavelength scan | 5.00 μl | 35 | d) Calculate value in accordance with the following calulating formula:

$$Cx = C1 + (C2-C1)*(Ax-A1)/(A2-A1)$$

C1 and C2: qantities of the standard.
A1 and A2: peak areas of the standard.
Cx and Ax: quantity and peak area of the sample.

e) The HPLC-FPS of Flos Lonicerae raw material:

The amounts of peaks are 8 at low limit and 11 at high limit, when the peak area is over $2.0 \times 10^6$.

This invention also provides a method for identifying with HPLC-FPS the composition of Fructus Forsythiae raw material, which further comprises the steps of: a) Using Phillyrin as the standard, and use the Chinese Fructus Forsythiae raw material as the sample; b) weighing exactly 375 mg of the powder of Fructus Forsythiae raw material, and prepare the sample solution further comprising the same steps as described above; c) performing the HPLC-FPS of Fructus Forsythiae raw material, under the conditions as described above; d) calculating the value of HPLC-FPS of Fructus Forsythiae raw material with the formula as decribed above; e) the HPLC-FPS of Fructus Forsythiae raw material:

The amounts of peaks are 11 at low limit and 14 at high limit, when the peak area is over $2.0 \times 10^6$.

This invention provides a method for identifying with HPLC-FPS the composition of Radix Scutellariae raw material, which further comprises the steps of: a) using Baicalin as the standard and use the Chinese Radix Scutellariae as the sample; b) weighing exactly 187 mg of the powder of Radix Scutellariae raw material and prepare the sample solution further comprising the same steps as described above; c) performing the HPLC-FPS of Radix Scutellariae raw material, under the conditions described above; d) calculating the value of HPLC-FPS of Radix Scutellariae's raw material with the formula as described above; e) the HPLC-FPS of Radix Scutellariae's raw material: The amounts of peaks are 22 at low limit and 25 at high limit, when the peak area is over $2.0 \times 10^6$.

This invention provides a method for identifying the composition of the drug substance of Flos Lonicerae and Fructus Forsythiae, which further comprises the steps of: a) using the Chlorogenic acid and Phillyrin respectively as standards, and the drug substance of Flos Lonicerar and Fructus Forsythiae as a sample; b) preparing the sample solution of the drug substance comprising the steps of: i) taking some Flos Lonicerar and Fructus Forsythiae, grind them into powder and then pass the 40 item of bolt; ii) weighing 107.5 mg of the powder and put it into an centrifuge tube; iii) adding 4 ml of methanol/water to a volute mixer and mix for 1 min; iv) Shaking the extracts ultrasonically for 15 min, centrifuge and take the upper solution; v) adding 4 ml of methanol/water and ultrasonically vibrate and extract the residue for another 15 min, centrifuge and take the upper clear solution; vi) washing the residue with 1.5 ml of methanol/water and combine it with the upper clear solution, scaling the sample solution in a 10 ml of flask; vii) filtering it with 0.45 μm filtration membrane before giving sample; c) performing the HPLC-FPS of the drug substance of Flos Lonicerae and Fructus Forsythiae, under the following conditions:

| Conditions of HPLC-FPS of Drug Substance | | | | | | |
|---|---|---|---|---|---|---|
| Chromatographic Column | Protecting Column | Floating Phase | Temperature | Inspector | Injection Volum | Run Time (min) |
| Inertsil ODS-3, 5 μm 4.6 mm*250 mm | phenomene x C18(ODS), 4 mm*3 mm ID | 1% acetic acid solution | room temperature | PDA210~400 nm whole wavelength scan | 20.00 μl | 35 | d) The HPLC-FPS of the drug substance of Flos Lonicerae and Fructus Forsythiae: the amounts of peaks are 18 at low limit and 23 ar high limit, when the peak area is over $2.0 \times 10^6$.

This invention provides a method for identifying with HPLC-FPS the composition of the drug substance of Radix Scutellariae, which further comprises the steps of: a) using Baicalin as the standard solution and use the drug substance of Radix Scutellariae as the sample solution; b) weighing exactly 20 mg of the powder of Radix Scutellariae and prepare the sample solution of the drug substance, further comprising the same steps as described above; C) performing the HPLC-FPS of the drug substance of Radix Scutellariae, under the conditions described above; d) the HPLC-FPS of the drug substance of Radix Scutellariae: The amounts of peaks are 4 at low limit and 5 at high limit, when the peak area is over $2.0 \times 10^6$.

This invention provides a method for identifying with HPLC-FPS the composition of the drug product, which further comprises the steps of: a) using Chlorogenic acid, Phillyrin and Baicalin as the standards and using the drug product with the batch number 00912 as the sample; b) weighing exactly 200 mg of the powder of drug product and prepare the sample solution of the drug substance, further comprising the steps described above; c) performing the HPLC-FPS of the drug substance of drug product, under the conditions described above; d) the HPLC-FPS of the drug substance of drug product: the amounts of peaks are 27 at low limit and 30 at high limit, when the peak area is over $1.95 \times 10^6$.

This invention provides a method for preparing a pharmaceutical composition comprising an extracts of Fructus Forsythiae and Flos Lonicerae. In an embodiment, the composition of Fructus Forsythiae and Flos Lonicerae was prepared with $CO_2$ supercritical fluid extraction under the control of homogeneous design.

This invention provides a method for preparation a composition comprising Fructus Forsythiae and Flos Lonicerae comprising the steps of: (a) preparing the extract with $CO_2$ supercritical fluid extraction with or without aqueous alcohol under the following conditions: 8.0–14.0 MP of pressure, at 32–40° C. of temperature for 1–3 hours; (b) breaking the materials into 20–60 mesh of reduction ratio; and (c) obtaining a 0.1–1% of extract rate.

In a separate embodiment, the extract of Fructus Forsythiae and Flos Lonicerae with subboiling aqueous are extracted under the following conditions: 80–95° C. of temperature and 1–3 hours of time.

This invention provides a method for purifying the sample solution with flocculating process, wherein the process was performed under the following conditions: the amount of flocculant is about 0.5 g–3.5 g/100 g of raw material; when the flocculant is added the specific gravity of the sample solution is 1.01–1.35. The temperature of the sample solution with the flocculant is 35–80° C. Concentration of aqueous alcohol is about 70–95%. The specific gravity of the sample solution is 1.1–1.3, when the aqueous alcohol is added.

This invention provides a method for determining with chromatography the content of Chlorogenic Acid in the Flos Lonicerae raw material comprising the steps of: a) using Chlorogenic acid as the standard solution and use Flos raw material as the sample solution; b) preparing the sample solution, further comprising the steps of: i) taking some Flos Lonicerae raw material, rub it into powder and pass the 40 item of bolt; ii) weighing up exactly 134 mg of the powder and put it into the centrifuge tube; iii) adding 4 ml of methanol/water to a volute mixer and mix for 1 minute; iv) Shaking the mixture and the extract ultrasonically 1 min., and then centrifuge it; v) taking the upper clear solution and add 4 ml of methanol/water to the residue and ultrasonic for 15 min, centrifuge it again; vi) washing the residue with 1.5 ml of methanol/water and combine it with the upper clear solution. Scale the sample solution in a 10 ml of flask; vii) filtering with 0.45 um of filtration membrane before giving sample; c) performing the HPLC of Chlorogenic Acid content of Flos Lonicerae raw material under the condition:

Conditions of HPLC-FPS of Raw Material Content

| Chromatographic Column | Protecting Column | Floating Phase | Temperature | Velocity of flow | Testing Wavelength | Run Time (min) |
|---|---|---|---|---|---|---|
| Inertsil ODS-3, 5μm 4.6 mm*250 mm | phenomene x C18(ODS) 4 mm*3 mm ID | methanol:water = 25:75 (contains 2% acetic acid) | room temperature | 1 ml/min | 280 nm | 35 |

This invention provides a method for preparing the above composition comprising extracts of Fructus Forsythiae and Flos Lonicerae comprising $CO_2$ supercritical fluid extraction containing the amount of aqueous alcohol entrainment, which is equal to the amount of 10%–90% $CO_2$.

This invention provides a method for embedding with $CO_2$ supercritical fluid extraction the supercritical extract of Fructus Forsythiae and Flos Lonicerae, wherein the supercritical extract was embedded with saturated solution of β-cyclodextrin. In an embodiment, the embedding rate is about 60%.

This invention provides a method for preparing the a composition comprising extracts of Fructus Forsythiae and Flos Lonicerae comprising the steps of: (a) embedding the supercritical extract of Fructus Forsythiae and Flos Lonicerae with saturated solution of β-cyclodextrin; (b) determinating the benzine content; and (c) granulating with solid dispersion technique. In an embodiment, the active ingredients of the supercritical extracts consisted of β-pinene, sabinene, α-pinene and linalool.

d) Content of Chlorogenic acid of Flos Lonicerae raw material:
Example: i) 1.85%; ii) 2.34%; iii) 1.51%. The result of the content is about: 1.05%–1.68%.

This invention provides a method for determining with chromatography the content of Phillyrin of Fructus Forsythiae raw material comprising the steps of: a) using Phillyrin as the standard solution and use Fructus Forsythiae raw material as the sample solution; b) taking 1.072 g of the powder of Fructus Forsythiae and prepare the sample solution comprising the steps as describe above; c) performing the HPLC of Fructus Forsythiae raw material under the following conditions:

Floating Phase: acetonitrile:water=28:72; d)
Content of Phillyrin of Fructus Forsythiae raw material:
Example: i) 0.21%; ii) 0.27%; iii) 0.17%. The result of the content is about: 0.10%–0.40%.

This invention provides a method for determining with chromatography the content of Baicalin of Radix Scutellariae raw material comprising the steps of: a) using Baicalin as a standard sample purchased from the Drug & Biological Product Test Agency and use Radix Scutellariae raw material as a sample; b) taking 100 mg of the powder of Radix Scutellariae and prepare the sample solution comprising the steps described above; c) performing the HPLC of Radix Scutellariae raw material under the following conditions-:Floating Phase: methanol: water (contains 2% acetic acid); and d) content of Baicalin of Radix Scutellariae raw material: Example: i) 4.21%; ii) 4.87%; iii) 3.81%. The result of the content is about 3.01%–4.47%.

This invention provides a method for determining with chromatography the Chlorogenic Acid content of drug substance of Fructus Forsythiae and Flos Lonicerae comprising the steps of: a) using the drug substance of Fructus Forsythiae and Flos Lonicerae as a sample; b) preparing the sample solution further comprising the steps of: i) weighing exactly 170.5 mg of the powder of drug substance of Flos Lonicerae and Fructus Forsythiae, and put it into the centrifuge tube; ii) adding 4 ml of methanol/water into a voluted mixer for 1 min; iii) Ultrasonically vibrate for 15 min, centrifuge and take the upper clear solution and ultrasonically vibrate the residue for another 15 min; iv) washing the residue with 4 ml of methanol/water and combine it with the upper clear solution, scaling the sample solution in a 10 ml of flask; vi) filtering it with the 0.45 um of filtration membrane before giving sample; c) calculating Chlorogenic Acid content of the sample according to the above-described formula and d) determining Chlorogenic Acid content of the drug substance: i) 2.52%; ii) 2.93%; iii) 2.15%. The result of Chlorogenic Acid content is about 1.00%–3.30%.

This invention provides a method for determining with chromatography the content of Phillyrin of the drug substance of Fructus Forsythiae and Flos Lonicerae comprising the steps of: a) weighing exactly 292 mg of the drug substance of Fructus Forsythiae and Flos Lonicerae; b) preparing the sample solution of extracts of Fructus Forsythiae and Flos Lonicerae, further comprising above steps; c) calculating Phillyrin content of the sample according to the same formula used in claim 1 and d) determining Phillyrin content of the drug substance: i) 0.66%; ii) 0.59%; iii) 0.75%; The result of Phillyrin content is about 0.2%–0.5%.

This invention provides a method to determine by chromatography the content of Baicalin in the drug substance of Radix Scutellariae comprising the steps of: a) weighing exactly 10 mg of the drug substance of Radix Scutellariae; b) preparing the sample solution of the drug substance of Radix Scutellariae, further comprising the above-described steps; c) calculating Baicalin content of the sample according to the above-described formula; d) determine Baicalin content of the drug substance: i) 93.4%; ii) 92.2%; iii) 91.3%; The result of Baicalin content is about: 90.01%–93.40%.

This invention provides a method for determining with chromatography the content of supercritical extract from of Fructus Forsythiae and Flos Lonicerae, comprising the steps of: a) determining the relative content under the following conditions: i) Gas Chromatographic: SE-54 elastic quarts capacity. Chromatographic column with a 30-meter length and a 0.32 mm inner diameter. Gasification room temperature of 250° C. Column temperature ranges from 50–230° C. rising 4° C./min controlled by procedure. ii) Gas carried to be Nitrogen with pre-column pressure of 0.7 kg/cm; iii) Column vollumn of 2 ml/min, giving sample quality of 0.4 ul. Testing machine FID. b) content of supercritical extract of Fructus Forsythiae and Flos Lonicerae: i) Contrast with the standard sample when tR=8.551 min, β-pinene can be obtained. When tR=12.926 min, linalool can be obtained. The absolute peak area is about 766933. ii) Contrast with the standard sample when tR=8.575 min, β-pinene can be obtained. When tR=12.919 min, linalool can be obtained. The absolute peak area is about 1138138. iii) Contrast with the standard sample when tR=8.539 min, β-pinene can be obtained. When tR=12.930 min, linalool can be obtained. The absolute peak area is about 906224. c) GC-Chromatograph is given in FIG. 8.

This invention provides a method for determining with GC-MS the supercritical extract of Fructus Forsythiae and Flos Lonicerae.

This invention provides a method for determining with GC-MS, wherein the values of GS-MS of the supercritical extract were shown in the following examples: β-pinene should be obtained at 8.551 min of RT (Retention Time). Linalool should be obtained at 12.926 min of RT. The absolute peak area is about 766933. β-pinene should be obtained at 8.575 min of RT. Linalool should be obtained at 12.919 min of RT. The absolute peak area is about 1138138. β-pinene should be obtained at 8.539 min of RT. Linalool should be obtained at 12.930 min of RT. The absolute peak area is about 906224.

This invention provides a formula of raw materials of the drug product comprising 1875 g of Flos Lonicerae, 3750 g of Fructus Forsythiae and about 1875 g of Radix Scutellariae.

This invention also provides an intermediate formula of the drug product, wherein the subject drug substances are presented in the following amounts: about 90–180 g of soft extract of Flos Lonicerae and Fructus Forsythiae, 10–60 g of supercritical extract of Flos Lonicerae and Fructus Forsythiae, 30–50 g of Radix Scutellariae extract and 23–125 g of excipients.

This invention provides a composition for preparing the drug product, wherein said constituents are presented in the following range: about 0.01 percent to about 99.99 percent of effective constituents, and about 99.99 percent to 0.01 percent of medical excipients.

This invention provides a composition, wherein said constituents are presented in the following formula: about 10 percent to 100 percent of Flos lonicerae, 10 percent to 100 percent of Fructus Forsythiae, and 10 percent to 100 percent of Radix Scutellariae. In an embodiment, the constituents are further composed of about 1.3 percent to 1.6 percent of Chlorogenic acid, 0.2 percent to 0.3 percent of Phillyrin and about 14.1 percent to 15.3 percent of Baicalin.

This invention provides a composition for inhibition of herpes I virus and herpes II virus comprising three herbal materials: Radix Scutellariae, Fructus Forsythiae and Flos Lonicerae.

EXPERIMENTAL DETAILS

Example 1

Preparation Techniques

This invention provides a unique formula of raw material for the composition of Flos Lonicerae, Fructus Forsythiae and Radix Scutellariae, wherein the formula comprises 1875 g of Flos Lonicerae, 3750 g of Fructus Forsythiae and 1875 g of Radix Scutellariae.

This invention provides an intermediate formula for the composition of drug substances. The formula comprises a range of 90–180 g extract of Fructus Forsythiae and Flos Lonicerae, a range of 30–50 g extract of Radix Scutellariae, a range of 10–60 g supercritical extract of Fructus Forsythiae and Flos Lonicerae and a range of 23–125 g of excipients.

This invention provides a composition further comprising supercritical extracts which includes β-pinene, sabinene, α-pinene, linalool.

This invention provides a method for preparing an extract of the Radix Scutellariae. The extraction includes the following steps: (a) Cut the raw material of Radix Scutellariae into small piece; (b) Put the small pieces through a process of reflux in ten times the volume of water; (c) Concentrate the soft extract at 80° C.; (d) Adjust the value of PH to 1.0–2.0 with 2 mol/L of chlorhydric acid; (e) Elute the residue to a 5.0 of PH value with water, and then eluting it to a 7.0 of PH value with 70% aqueous alcohol; (f) Dry it at lower temperature; (g) Produce an extract of Radix Scutellariae.

This invention provides a method for preparing an extract of Fructus Forsythiae and Flos Lonicerae with sub-boiling aqueous extraction. The method comprises the following steps: (a) Take the decoction dregs of Fructus Forsythiae and Flos Lonicerae after extracted with $co_2$ supercritical fluid and add 10 times of water; (b) Put the mixture into a process of agitation and dynamic extraction for 2 hours and filtration; (c) Concentrate the decoction to about 1.03 of relative density at 25° C.; (d) Cool the filtrate and add flocculating agent; (e) filtration and concentrate the flocculation solution to about 1.1 to 1.2 of relative density at 25° C. (f) Add 80% of aqueous alcohol solution to sedimentation; (g) After concentrating, obtain the aqueous extract of Fructus Forsythiae and Flos Lonicerae.

This invention provides a method of flocculation and alcohol sedimentation for the sub-boiling aqueous extracts of Fructus Forsythiae and Flos Lonicerae, wherein the method was conducted under the following conditions: (a) the ratio of decoction: add 0.5 g–3.5 g of flocculating agent to 100 g of raw material; (b) Filtrate the decoction to about 1.01 to 1.35 of relative density; (c) Keep the temperature at 35–80° C. (d) Add a 70–95% of alcohol concentration; (d) Keep a 1.1–1.3 of specific gravity while alcohol is added.

This invention provides a method for preparing an extract of Fructus Forsythiae and Flos Lonicerae with $co_2$ supercritical fluid extraction comprising the following steps:

I) $co_2$ supercritical fluid extraction without entrainment: (a) Break the mixture of Fructus Forsythiae and Flos Lonicerae; (b) Put the broken mixture through a process of extraction in an extractor under the 8.0–14.0 MP of pressure; (c) Produce the extract of Fructus Forsythiae and Flos Lonicerae.

II) $co_2$ supercritical fluid extraction with entrainment: (a) Break the mixture of Fructus Forsythiae and Flos Lonicerae; (b) Put the broken mixture through a extraction process under 8.0–14.0 MP of pressure; (c) Add 90–95% aqueous alcohol, equal to a 10%–90% the volume of $CO_2$, to the extractor; (d) Obtain the extract of Fructus Forsythiae and Flos Lonicerae.

This invention provides a method for embedding the $CO_2$ supercritical extracts of Fructus Forsythiae and Flos Lonicerae with saturated aqueous solution of β-cyclodextrin (β-CD). Wherein the method comprises the following steps:
(a) Prepare the inclusion compound: (i) take respectively 6.0 g, 8.0 g, 10.0 g of β-CD and put it into a flask with 150 ml of volume. (ii) Add the β-CD respectively to distilled water with a ratio of 1:6. (iii) Heat the liquid to dissolution, and then decrease the temperature. (iv) Put the flask on a magnetic agitator. (v) Slowly inject 1 ml of Benzin to the β-CD solution with a 1 ml of injector. (vi) Agitate and keep it in cold storage. (vii) Filter and collect the inclusion compound, and then dry the solution of inclusion compound to the powder at 60° C. for 2 hours;
(b) Determine the content of benzin of inclusion compound, wherein the method supposed to comprises the following steps: (i) Take the inclusion compound and put it into a 500 ml of flask. (ii) Add 200 ml of distilled water and connect the flask with an extractor of benzin, according to the operation procedure in the Appendix 6 of Chinese Pharmacopeia, 1995. (iii) Record the content of benzin; and
(c) Determine the black recovery rate of benzin This invention provides a method for embedding the extract of Fructus Forsythiae and Flos Lonicerae with about a 60% of the embedding rate.

This invention provides a method for preparing the drug product of Flos Lonicerae, Fructus Forsythiae and Radix Scutellariae. Wherein the said method is consisted of: (a) Draw up a formula of raw materials, including Flos Lonicerae to Fructus Forsythiae to Radix Scutellariae (1:2:1); (b) Prepare the extract of Radix Scutellariae; (c) Prepare the extracts of Fructus Forsythiae and Flos Lonicerae with sub-boiling aqueous and with $CO_2$ supercritical fluid respectively; (d) Embed the $CO_2$ supercritical extracts of Fructus Forsythiae and Flos Lonicerae with saturated aqueous solution of β-cyclodextrin; (e) Determine the benzine content in inclusion compound; (f) The extract of Radix Scutellariae and the carrier were subjected to a process of granulating with solid dispersion technique.

This invention provides a composition comprising 0.01% to 99.99% of effective constituents and 99.99% to 0.01% of medical dressing.

FORMULA EXAMPLES

Example 1

To obtain a 3% of extract rate of the drug substance, the formula is as follows: 90 g of soft extract of Flos Lonicerae and Fructus Forsythiae, 30 g of extract of Radix Scutellariae, 15 g of supercritical extract of Fructus Forsythiae and Flos Lonicerae, and 24 g of excipients.

Example 2

To obtain a 4% of extract rate of the drug substance, the formula is as follows: 120 g of soft extract of Flos Lonicerae and Fructus Forsythiae, 30 g of extract of Radix Scutellariae, 15 g of supercritical extract of Fructus Forsythiae and Flos Lonicerae, and 29 g of excipients.

Example 3

To obtain 5% of extract rate of the drug substance, the formula is as follows: 150 g of soft extract of Flos Lonicerae and Fructus Forsythiae, 30 g of extract of Radix Scutellariae, 15 g of supercritical extract of Flos Lonicerae and Fructus Forsythiae, and 34 g of excipients.

Example 4

To obtain a 6% of extract rate of the drug substance, the formula is as follows: 180 g of soft extract of Flos Lonicerae and Fructus Forsythiae, 30 g of extract of Radix Scutellariae, 15 g of supercritical extract of Fructus Forsythiae and Flos Lonicerae, and 40 g of excipients.

Supercritical Fluid Extraction Technology

1. Fluid Extraction

Carbon dioxide is considered the best gas medium to be used in this experiment. The CO2 has the property of allowing quick dissolution of the three herbs used in this process to easily obtain the components needed for the invention. Therefore, the $CO_2$ extracting technology has been adapted in order to obtain and separate the effective ingredients of the raw materials used in the experiment.

2. Carrying Solvent Extraction

Some carrying solvents of the $CO_2$, such as ethanol, can help in the extraction of the components found in the raw materials used for this invention. Ethanol: CO2=0.1–0.9:1.

3. Main Parameters

A. Pressure

Supercritical fluid can be pressed greatly. When the temperature is constant, the density of the supercritical fluid increases with pressure and the ingredient solubility in fluid is improved simultaneously.

B. Temperature

If pressure is constant, the extracting effect is heightened by high temperature.

C. Time

Usually, the longer the time, the more extract would be obtained from the process. Still, it is possible that some unnecessary matters could be extracted out and then more $CO_2$ is consumed.

D. Materials

The higher the reduction ratio (refinement of the powder) the more it can be used to promote the diffusion of the materials. The positive effect of having a high reduction ratio can be damaging if the powder is too thin.

E. Carrying solvent

Usually, carrying solvents are more useful in order to get more substance.

4. Experiment

TABLE 1

| | Materials | | |
|---|---|---|---|
| Name | Producing Area | Seller | Appraisal |
| Radix Scutellariae | | | |
| Flos Lonicerae | Shandong | ShanghaiHuaYu | Eligible |
| Fructus Forsythiae | Henan | ShanghaiHuaYu | |
| $CO_2$ | Shanghai | Wujing Chem | Plant Food Grade |

TABLE 2

| Supercritical Extraction Equipment | |
|---|---|
| Sepecification | Producer |
| 200 ml | Nova Co. Switzerland |
| 20 L | Jiangsu, China |
| 100 L | Shanghai, China |

C. Experiment Process

The sack, including the smashed Flos Lonicerae and the Fructus Forsythiae were put into the extractor. The solution was kept under the following conditions: 8.0–14.0 MP of pressure and 32–40° C. of temperature for one hour. The extracts were analyzed with GC.

5. Conditions

Herbs Flos Lonicerae and Fructus Forsythiae were processed by supercritical $CO_2$ extraction under the following conditions: 8.0–14.0 MP of pressure and 32–40° C. of temperature for one hour. GC tested the product to be steady. Physiology research proved its properties as an anti-virus. The effectiveness of the final product was improved with the use of the new technique of extraction.

Flocculating Test

The separation technology is the key to raise the level of traditional Chinese medicine. The refining method usually is ethanol subsiding and the flocculating method.

1. The Methods and Principles of Refining Traditional Chinese Medicine

The technology of ethanol subsiding is usually used to refine Chinese medicine preparations. One of the principles of the ethanol subsiding is that some effective components of traditional Chinese medicines can be dissolved not only in water but also in ethanol. The unsolvable substances in ethanol can be subsided in a mixed solution of water and ethanol in order to refine the product and improved its quality.

In the Flocculating process, a flocculating agent is used to refine traditional Chinese medicine. An example of a flocculating agent is the Chitosan, which is added to the extracting solution. Colloid pellets were cleared away in an absorbing matter, such as protein and mucilage, and then were filtrated to refine the solution. The extracting solution of the traditional Chinese medicine has many components, such as polymer, mucus, protein, and starch. When Chitosan is added, big pellets were cleared away by the absorbing function of the bridge and the electric neutralization. This technology has many advantages: fewer raw materials are used, the equipment is simple and production costs are lower. The speed of flocculating is fast and less production time is needed.

2. Properties of Flocculating Agent

Chitosan is a kind of linear ploycarbohydrate, a good flocculating agent of natural polyme instead of the synthetic one. Its chemical name is poly [β-(1,4)-2-amino-2-deoxy-D-glucopyranose]. Chitosan is a natural polymer that is safe for consumption. The process of preparing shell material to render Chitosan is presented in Below

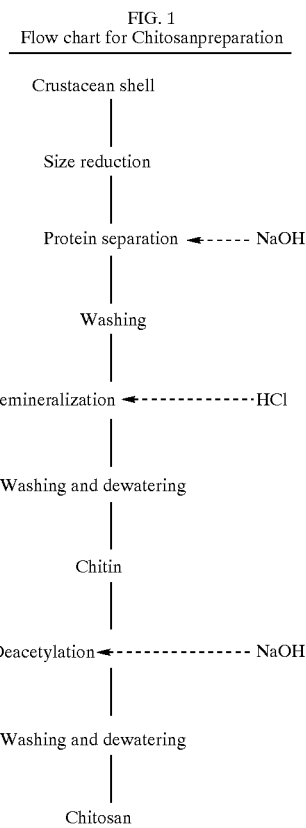

FIG. 1
Flow chart for Chitosanpreparation

Preparation of the Drug Product

The mixed material of Flos Lonicerae and Fructus Forsythiae were extracted with ten times of the volume of water. The decoction was filtrated and the extracting solution was concentrated and flocculated with Chitosan. Ethanol was added to this concentrated solution. The ethanol solution was filtrated and evaporated as well. The method was designed as follows:

1. Well-Distributed Design: (see Table 3)

TABLE 3

Test of well-distributed design

| No | Extracting Temperature (° C.) | Time (h) | Flocculating agent (g/100 g) | Flocculating Temperature (° C.) | Concentration (ml/g material) |
|---|---|---|---|---|---|
| 1 | 75.0 | 1.5 | 1.5 | 65.0 | 3.5 |
| 2 | 75.0 | 2.0 | 2.5 | 50.0 | 3.5 |
| 3 | 75.0 | 2.5 | 3.5 | 35.0 | 3.5 |
| 4 | 80.0 | 3.0 | 0.5 | 80.0 | 2.5 |
| 5 | 80.0 | 1.5 | 2.5 | 50.0 | 2.5 |
| 6 | 80.0 | 2.0 | 3.5 | 35.0 | 2.5 |
| 7 | 85.0 | 2.5 | 0.5 | 80.0 | 1.5 |
| 8 | 85.0 | 3.0 | 1.5 | 65.0 | 1.5 |
| 9 | 85.0 | 1.5 | 3.5 | 35.0 | 1.5 |
| 10 | 90.0 | 2.0 | 0.5 | 80.0 | 0.5 |
| 11 | 90.0 | 2.5 | 1.5 | 65.0 | 0.5 |
| 12 | 90.0 | 3.0 | 2.5 | 50.0 | 0.5 |

TABLE 4

Results of well-distributed

| No | ratio of product (%) | Percent of Chlorogenic acid (%) | clearness of solution |
|---|---|---|---|
| 1 | 17.5 | 1.19 | +++ |
| 2 | 17 | 1.18 | ++ |
| 3 | 17 | 1.09 | + |
| 4 | 18.5 | 1.20 | ++++ |
| 5 | 17.5 | 1.10 | + |
| 6 | 17 | 1.26 | + |
| 7 | 16.5 | 1.21 | ++++ |
| 8 | 17 | 1.29 | – |
| 9 | 17 | 1.34 | – |
| 10 | 13 | 1.41 | – |
| 11 | 13 | 1.40 | + |
| 12 | 13 | 1.35 | – |

2. The Effect of Extracting Temperature

TABLE 5

Effect of extracting temperature

| Time (h) | Temperature (° C.) | Chlorogenic acid (mg/ml) |
|---|---|---|
| 2 | 80 | 0.380 |
| 2 | 85 | 0.390 |
| 2 | 90 | 0.409 |
| 2 | 95 | 0.362 |
| 3 | 95 | 0.334 |
| 2.5 | 90 | 0.392 |

The extracting temperature affected the amount of Chrorogenic acid. The best condition to extract the material is at 90° C. for two hours.

3. The Effect of Flocculating Agent

TABLE 6

Effect of flocculating agent

| Flocculating agent (g/100 material) | Clearness of solution | Precipitate form |
|---|---|---|
| 0.5 | Muddy | Fine |
| 1.0 | Muddy | Fine |
| 1.5 | Clear | Fine |
| 2.0 | Clear | Thick |
| 2.5 | Clear | Fine |
| 3.0 | Muddy | Fine |
| 3.5 | Muddy | Fine |

The amount of flocculating agent mainly affects the clearness of the solution. When the amount of flocculating agent varies, for example to a 0.5 g/100 g or 3.5 g/100 g of raw material, the solution could become muddy. While the amount of flocculating agent is suitable, the solution is clear. The reason is because the flocculating function is absorbing the bridge and the electric neutralization. If the amount of flocculating agent is reduced, the flocculating pellets cannot be formed between colloid. If the amount of flocculating agent is increased, then the Chitosan surrounds the colloid and the possibility of absorbing the bridge is lost, so the colloid is stable. When Chitosan covers a part of the colloid surface is possible to obtain the best results from flocculating. So the scope of flocculating agent is 1.5–2.5 g/100 g material.

4. The Effect of Flocculating Temperature

The flocculating temperature mainly affects the clearness of the solution and precipitates it form. When the temperature is higher, the solution is muddy, but the pellet is thick. When the temperature is lower, the solution is clear, but the pellet is thinner. Therefore, the most appropriate temperature to be used in this experiment is 50° C.

TABLE 7

Effect of Flocculating Temperature

| Temperature (° C.) | Clearness of solution | Precipitate form |
|---|---|---|
| 20 | Clear | Fine |
| 30 | Clear | Fine |
| 40 | Clear | Fine |
| 50 | Clear | Thick |
| 60 | Clear | Thick |
| 70 | Muddy | Thicker |
| 80 | Muddy | Thicker |

5. The Effect of the Solution Concentration

The concentration affects mainly the ratio of product. With the increasing of the concentration, the ratio of product is lower. For example, when the ratio of material and solution is equal to 2:1 (g/ml), the obtained ratio is the lowest. At the more concentrated solution, the Chitosan agent is more difficult to disperse in the decoction process and it is also easier to coagulate into small particles.

6. The Across Test

The amount of Chitosan, the quality and ratio of product and the effects of the extracting temperature were studied based on well-distributed tests. In order to purify and reduce the ratio of product, further studies were made of the amount and concentration of Chitosan, and the concentration of ethanol on the quality of product.

TABLE 8

Across Design for the technique of drug product

| NO. | Flocculant g/100 g | The 2$^{nd}$ concentration(ml/100 g) | Concentration of ethanol (%) | Material/solution (G/ml) |
|---|---|---|---|---|
| 1 | 1.5 | 10 | 90 | 1:0.5 |
| 2 | 1.5 | 15 | 80 | 1:0.8 |
| 3 | 1.5 | 20 | 70 | 1:1.0 |
| 4 | 2.0 | 10 | 80 | 1:1.0 |
| 5 | 2.0 | 15 | 70 | 1:0.5 |
| 6 | 2.0 | 20 | 90 | 1:0.8 |
| 7 | 2.5 | 10 | 70 | 1:0.8 |
| 8 | 2.5 | 15 | 90 | 1:1.0 |
| 9 | 2.5 | 20 | 80 | 1:0.5 |

During the trial period, the method of flocculating was combined with ethanol subsiding. Most of the components, such as proteins and carbohydrates, had been removed but other components were retained by flocculation. Most of the polysaccharides and the Chitosan had been removed by ethanol subsiding.

TABLE 9

The result of Across Design for the technique of drug product

| No | Flocculant g/ 100 g | The concentration (ml) | ethanol (%) | Material solution (g:ml) | ratio of product (%) | percent of Chlorogenic acid(%) |
|---|---|---|---|---|---|---|
| 1 | 1.5 | 10 | 90 | 1:0.5 | 4.25 | 1.88 |
| 2 | 1.5 | 15 | 80 | 1:0.8 | 5.25 | 0.86 |
| 3 | 1.5 | 20 | 70 | 1:1.0 | 9.25 | 1.38 |
| 4 | 2.0 | 10 | 80 | 1:1.0 | 4.13 | 1.65 |
| 5 | 2.0 | 15 | 70 | 1:0.5 | 8.50 | 1.87 |
| 6 | 2.0 | 20 | 90 | 1:0.8 | 5.88 | 1.63 |
| 7 | 2.5 | 10 | 70 | 1:0.8 | 4.00 | 1.62 |
| 8 | 2.5 | 15 | 90 | 1:1.0 | 2.63 | 1.34 |
| 9 | 2.5 | 20 | 80 | 1:0.5 | 6.13 | 1.61 |

With the increase in the amount of Chitosan used in the second concentration of solution and the concentration of ethanol, the ratio of product decreased. The process of refining traditional Chinese medicine consists in having 100 g material extracted in ten times the amount of water at 90° C. for 2 hours. After being filtrated and concentrated to 80 ml (the density is 1.124), 133 ml 1.5%, the flocculating agent was added. Stirred for 5 minutes, centrifugalized and concentrated to 16 ml (the density is 1.26). 95% ethanol was added until the percentage reached 85. Once filtrated and concentrated, the ratio of product was 4–5%. The percent of Chlorogenic acid was 1.55%.

Example 2

Pharmacological Studies

The pharmaceutical compositions comprising the extract of Flos Lonicerae, Fructus Forsythiae and Radix Scutellariae described in this invention are effective for the inhibition of influenza virus and parainfluenza virus, herpes I virus and herpes II virus.

1. Anti-Virus Test

A. Anti-Virus Test in Vivo

The extract of Flos Lonicerae, Fructus Forsythiae and Radix Scutellariae, both with supercritical fluid extraction and sub boiling aqueous extraction, were used as test drugs. A chemical drug known as Ribavirin, Batch No. 980606, was positively controlled with the extract mentioned above. Influenza virus A3, parainfluenza virus I (HVJO), herpes I virus, herpes II virus (HSV-I, II), and Hep-2 cells (human epithermoid carcinoma) were used as test materials.

In the invention, the cytotoxic test was conducted with clonal Hep-2 cells of human epithermoid carcinoma. The decoction was diluted with the culture solution of Eagles in multiple proportions. The culture solution of Hep-2 cell cultured in 96 pores of microculture plate was discharged and 100 ul of a different dilution was added to the decoction. The normal cells were controlled with the cultured cells. The cultured plate was laid in a $CO_2$ incubator at 37° C. for 3 days. The extract toxicity for the cells was delimited in accordance with the minidilution titer without the degeneration of cells. 50% of the toxic concentration ($CC_{50}$) was calculated with the method of Reed-Mucnch.

A total of 50 ul of different viral solution was inoculated to the cell plate and was put into $CO_2$ incubator for absorption. 100 ul decoction of different dilution was added to the inoculated plate and observed in $CO_2$ incubator at 37° C. for 3 days. The test group was compared to the virus auto-control group, to the positive control group with Ribavirin, and to the normal cell control group.

The result of the test showed that there was a difference for anti-virus effect between different sites of extraction (Table 10). The extracts of Flos Lonicerae, Fructus Forsythiae and Radix Scutellariae with supercritical fluid extraction had a significant inhibition for influenza virus and parainfluenza virus. The extracts of Flos Lonicerae, Fructus Forsythiae and Radix Scutellariae with sub-boiling aqueous extraction had also a certain inhibition degree for influenza virus, herpes I virus and herpes II virus (HSV-I, II). (Table 11)

TABLE 10

Effect for anti-virus in different sites of extraction

| | | $EC_{50}$ (crude drug µg /ml) | |
|---|---|---|---|
| Virus | Ribavirin (125 µg/ml) | Supercritical Extraction Site | Sub-boiling Aqueous Extraction Site |
| $A_3$ | + | 83.93 (6.7) | 236.6 (9.4) |
| HVJ | + | 167.5 (3.4) | – |
| HSV-I | + | – | 561.2 (4.0) |
| HSV-II | ± | – | 472.1 (4.7) |

TABLE 11

Inhibitory effect of different drug products on cytopathy induced by virus

| | | $EC_{50}$ (crude drug µg /ml) (IT) | | | |
|---|---|---|---|---|---|
| Virus | Ribavirin (125 µg/ml) | No.25 | No.26 | No.27 | SHL tablet |
| $A_3$ | + | 4.7 (4.8) | 4.7 (4.8) | 3.3 (6.8) | 4.7 (4.8) |
| HVJ | + | 4.7 (4.8) | 4.7 (4.8) | 3.3 (6.8) | 4.7 (4.8) |
| RSV | + | 11.1 (2.0) | 11.1 (2.0) | 6.7 (3.4) | 11.1 (2.0) |
| HSV-I | + | – | 11.1 (2.0) | 6.7 (3.4) | – |
| HSV-II | + | – | 11.1 (2.0) | 6.7 (3.4) | – |

Note:
"+": effective, "–": ineffective
SHL (Shuanghuanglian) tablet is a previous product produced with different techniques.
No.25, 26 and 27 are the samples of drug product produced with new techniques.

B. Anti-Virus Test in Vivo

TABLE 12

Effect of different drug products on Virus Pneumonia induced by influenza

| Groups | Dosage (g/kg) | Mice (n) | Lung index (X ± SD) | Inhibitive rate (100%) | P value |
|---|---|---|---|---|---|
| Infection control | – | 10 | 1.54 ± 0.25 | | |
| Normal control | – | 10 | 0.91 ± 0.07 | | <0.01 |
| Ribavirin | 0.07 | 10 | 1.16 ± 0.15 | 24.68 | <0.01 |
| SHL tablet | 33.0 | 10 | 1.27 ± 0.19 | 17.53 | <0.05 |
|  | 16.5 | 8 | 1.33 ± 0.17 | 13.64 | >0.05 |
| No.25 | 33.0 | 10 | 1.33 ± 0.13 | 13.64 | <0.05 |
| No.26 | 33.0 | 10 | 1.33 ± 0.8 | 13.64 | <0.05 |
|  | 16.5 | 10 | 1.36 ± 0.18 | 11.69 | >0.05 |
| No.27 | 33.0 | 10 | 1.25 ± 0.21 | 18.83 | <0.01 |
|  | 16.5 | 8 | 1.32 ± 0.20 | 14.28 | <0.05 |

Note:
SHL (Shuanghuanglian) tablet is a previous drug product produced with different techniques.
No.25, 26 and 27 were the samples of drug products produced with the new techniques.

2. Anti-Anaphylaxis Test

A three-color guinea pig was used in the following experiment. The extracts of Flos Lonicerae, Fructus Forsythiae and Radix Scutellariae, both with supercritical fluid extraction and with subboiling aqueous extraction, were used as test drugs. Ebalin, an antihistamine, was used as the control drug.

The ileum of a guinea pig was taken and hung on a Magnus' bath. The basic contraction frequency of the ileum was recorded with the MacLab method. There was a total of four groups involved in this experiment: the histamine alone, the histamine plus Ebalin, the histamine plus the supercritical extract of Flos Lonicerae, Fructus Forsythiae and Radix Scutellariae, and the histamine plus sub-boiling aqueous extract. The test curves were respectively recorded after the administration of the histamine and the other test drugs. The inhibitory rate and exciting rate were calculated with the following formula:

$$\text{Inhibitory/exciting rate (\%)} = \frac{\text{Normal mean wave amplitude} - \text{post-test mean wave amplitude}}{\text{Normal mean wave amplitude}} \times 100\%$$

The results of the test demonstrated that supercritical extract and sub-boiling aqueous extract, and the different products of Flos Lonicerae, Fructus Forsythiae and Radix Scutellariae had significant inhibition for ileum contraction induced by histamine. (Table 13, Table 14)

TABLE 13

Inhibitory effect of the different extracts on histamine in guinea pig

| Group | Concentration (g/ml) | Inhibition/excitation (%) |
|---|---|---|
| Histamine | $3.3 \times 10^{-6}$ | 271 ± 42 |
| Histamine + Ebalin | $3.3 \times 10^{-6} + 1 \times 10^{-3}$ | 181 ± 32** |
| Histamine + supercritical supercritical extract | $3.3 \times 10^{-6} + 1 \times 10^{-3}$ | 234 ± 59* |

TABLE 13-continued

Inhibitory effect of the different extracts on histamine in guinea pig

| Group | Concentration (g/ml) | Inhibition/excitation (%) |
|---|---|---|
| Histamine + sub-boiling aqueous extract | $3.3 \times 10^{-6} + 1 \times 10^{-3}$ | 203 ± 96* |

Note:
*P < 0.05, **P < 0.01, in comparison with control group

TABLE 14

Inhibitory effect of the different drug products on histamine in guinea pig

| Group | Concentration (g/ml) | Inhibition/excitation (%) |
|---|---|---|
| Histamine | $3.3 \times 10^{-6}$ | 235.29 ± 35.30 |
| Histamine + Ebalin | $3.3 \times 10^{-6} + 1 \times 10^{-6}$ | 133.81 ± 40.55** |
| Histamine + No.21 | $3.3 \times 10^{-6} + 1 \times 10^{-3}$ | 237.75 ± 52.08 |
| Histamine + No.22 | $3.3 \times 10^{-6} + 1 \times 10^{-3}$ | 181.45 ± 35.46 |
| Histamine + No.23 | $3.3 \times 10^{-6} + 1 \times 10^{-3}$ | 220.98 ± 46.39 |
| Histamine + No.24 | $3.3 \times 10^{-6} + 1 \times 10^{-3}$ | 179.21 ± 25.00* |
| Histamine + No.29 | $3.3 \times 10^{-6} + 1 \times 10^{-3}$ | 229.93 ± 28.08 |

Note:
*P < 0.05, **P < 0.01, compared with control group;
No.21, 22, 23 and 24 are the samples of drug product, which are produced with new techniques.
No.29 is a drug product produced with previous techniques.

3. Anti-Inflammation Test 3.1 Effect for Leukotaxis

Rats were used as test animals. The supercritical extract of Flos Lonicerae, Fructus Forsythiae and Radix Scutellariae, was dissolved with dimethyl sulfoxide, diluted with RPMI-1640 and used as the test drug.

The inhibitory effect of supercritical extract and sub-boiling aqueous extract for leukotaxis was observed in the test of rats through the following steps: 1) Preparing $10^9$/ml of leukocytic suspension. 2) Dissolving 4 mg of agarose into 0.5 ml of distilled water and cooling it to 37° C. of temperature, and then mixing it with RPMI-1640. 3) Taking 0.1 ml of the solution of agarose and 0.1 ml of leukocytic suspension. 4) Injecting the mixed solution of leukocyte and agarose prepared above into a cultured plate of 96 pores, 2 ul for each. 5) Dividing the test group in four groups with normal saline (NS), Chemitactic agent, Dimethyl sulfoxide (DMSO) and test drugs (three doses). 6) Determining the distance of leukocytic movement with position finder under the microscope and calculating mobile area. 7) Analyzing the data with T test.

The result showed that the supercritical extract and sub-boiling aqueous extract of Flos Lonicerae, Fructus Forsythiae and Radix Scutellariae had a significant effect in the inhibition for the leukotaxis. It suggested that the different extracts and the drug products of Flos Lonicerae, Fructus Forsythiae and Radix Scutellariae had also obvious inhibitory effect for inflammation. (Table 15, Table 16)

TABLE 15

Inhibitory effect of the different extracts on Leukotaxis

| Group | Dosage (mg/ml) | Area of Leukocyte movement (mm²) |
|---|---|---|
| Normal Saline | — | 17.0 ± 11.1 |
| FMLP | 5 nM | 229.2 ± 191.9# |
| DMSO |  | 159.6 ± 127.1# |
| supercritical | 1.0 | 128.6 ± 147.9 |
| extract | 0.1 | 22.8 ± 27.2▽ |
|  | 0.01 | 18.2 ± 11.9▽ |
| sub-boiling aqueous | 1.0 | 27.5 ± 22.1* |
| extract | 0.1 | 28.1 ± 25.6* |
|  | 0.01 | 11.9 ± 9.9* |

Note:
DMSO: Dimethyl sulfoxide
P < 0.05, in comparison with the Normal Saline group
*P < 0.05, in comparison with the FMLP group
▽P < 0.05, in comparison with the DMSO group

TABLE 16

Inhibitory effect of the drug products with different technique on the Leukotaxis

| Group | Dosage (mg/ml) | Area of Leukocyte movement (mm²) |
|---|---|---|
| Normal Saline | — | 2.08 ± 0.51 |
| FMLP | 5 nM | 7.89 ± 4.92# |
| Dimethyl sulfoxide |  | 7.87 ± 4.12## |
| Normal Serum |  | 7.71 ± 3.52## |
| No. 22 | 1.0 | 7.94 ± 2.74* |
|  | 0.1 | 7.06 ± 3.44* |
|  | 0.01 | 7.27 ± 2.62 |
| No. 24 | 1.0 | 3.42 ± 1.9* |
|  | 0.1 | 5.3 ± 2.43 |
|  | 0.01 | 6.01 ± 2.67 |
| No. 29 | 1.0 | 6.14 ± 2.31 |
|  | 0.1 | 6.84 ± 3.11 |
|  | 0.01 | 6.08 ± 3.13 |
| Drug-serum 22 | 40 min | 4.55 ± 1.55▽ |
| Drug-serum 22 | 80 min | 4.61 ± 2.26 |
| Drug-serum 24 | 40 min | 5.91 ± 2.21 |
| Drug-serum 24 | 80 min | 4.48 ± 1.20▽ |

Note:
P < 0.05, ##: P < 0.01, compared with Normal Saline group
*P < 0.05, compared with FMLP group
▽P < 0.05, compared with DMSO group.
No. 22 or No. 24 is the samples of drug products produced with new techniques; No. 29 is a previous drug product produced with different techniques.

Example 3

Studies of Pharmacodynamics

In the studies in vitro, the drug product of Flos Lonicerae, Fructus Forsythiae and Radix Scutellariae, which was made with extraction and refined production, can completely inhibit the replication of four kinds of virus at 50 mg of concentration of the drug. The results of the anti-virus test showed that the test drug had clear anti-virus effect in vitro and had protective effect for the infective mice in vivo. The result of bacteriostatic test showed that the test drug had inhibition in varying degree for six kinds of bacteria, such as *Staphylococcus aureus*, etc. in vitro and had obvious protective effect for the mice after infection with *Staphylococcus aureus* and Diplococcus pneumoniae.

1. Bacteriostatic Effect of the Drug Product in Vitro

Test Materials

Sample: The drug product (Diantic Tablet) was provided by National Engineering Research Center for Traditional Chinese Medicine of China. Batch number: 20000801. Dosage: 0.7 g/tablet (equal to 15 crude drugs), 2 tablet/time, three times per day.

Strain: *Staphylococcus aureus*, Shigella shigae, *Bacillus coli*, *Pseudomonas aeruginosa* and *Bacillus cereus*, which were purchased from Institute of Materia Medica, Chinese Academy of Medical Science.

Method: Doubling Dilution Method

Prepare the drug product of Flos Lonicerae, Fructus Forsythiae and Radix Scutellariae in a 10% of stock solution. Dilute the test solution with the bacteria, which was cultured in bouillon for 8 hours, into 0.1% of solution with a bouillon without asepsis. And then take 0.1 ml of the dilution and respectively put it into a series of test tubes, which are contained the drug product and double diluted with an aseptic bouillon. Put the test solution into an incubator at 37° C. for 24 hours and observe the test result. Take other test tubes to blank control (with the bacteria and without test drug) and self control (with test drug and without the bacteria). Take each strain to parallel test.

Result:

The results showed that the drug product could exert inhibitory effects in vitro for gram-positive cocci, gram-positive bacilli, and gram-negative bacilli in varying degrees and illustrated that its anti-microbial spectrum is broad. The bacteriostasic effects of the drug product are shown in Table 17.

TABLE 17

Bacteriostasic Effects of the drug product

| | Drug dilution rate | | | | | | | | | | |
|---|---|---|---|---|---|---|---|---|---|---|---|
| Group | Original | 1:2 | 1:4 | 1:8 | 1:16 | 1:32 | 1:64 | 1:128 | 1:256 | self control | blank control |
| *Staphylococcus aureus* | − | − | − | − | − | − | − | + | + | − | + |
| *Shigella shigae* | − | − | + | + | + | + | + | + | + | − | + |
| *Diplococcus pneumoniae* | − | − | − | − | − | + | + | + | + | − | + |
| *Bacillus coli* | − | − | − | − | − | − | + | + | + | − | + |
| *Bacillus cereus* | − | + | + | + | + | + | + | + | + | − | + |
| *Bacillus pyocyaneus* | − | − | − | − | + | + | + | + | + | − | + |

"−": no inhibition;
"+": inhibition

2. Effect of the Drug Product for *Staphylococcus Aureus* and Diplococcus Pneumoniae in Mice Strain: *Staphylococcus aureus* and *Diplococcus pneumoniae*, which were purchased from Chinese Academy of Preventive Medical Science.

Animal: The Kunming mice were provided by Institute of Materia Medica, Chinese Academy of Medical Science.

Method: 80 health mice (18–22 g) with equal number of males and females were randomly divided into four groups, 20 mice for each group. The *Staphylococcus aureus* with Gastric Mucin ($10^8$/ml) were intraperitoneally injected to the mice, in a ratio of 0.2 ml/10 g weight for test group and 0.5 ml/20 g weight for the control group. The mice were continuously injected for five days and observed for seven days. Their dietary activities and the number of death were recorded. Other 80 mice were divided into groups and take the same method to test. The Diplococcus pneumoniae were intraperitoneally injected to the mice in a ratio of $1.2 \times 10^8$/ml and 1.2 ml/10 g weight. The result showed that the drug product of Flos Lonicerae, Fructus Forsythiae and Radix Scutellariae (Diantic tablet) had protective effect for the mice with the infection of *Staphylococcus aureus* and Diplococcus pneumoniae. The test result was showed in the Table 18.

TABLE 18

Effects of the drug product for the mortality of bacteria

| Group | Dosage | Animal | *Staphylococcus aureus* Death No. | Mortality | P | *Diplococcus pneumoniae* Death No. | Mortality | P |
|---|---|---|---|---|---|---|---|---|
| Blank | — | 20 | 18 | 90 | | 17 | 85 | |
| Test 1 | 0.72 | 20 | 10 | 50 | <0.05 | 9 | 45 | <0.05 |
| Test 2 | 1.44 | 20 | 0 | 40 | <0.01 | 8 | 40 | <0.01 |

3. Inhibitory Effect of the Drug Product for the Influenza Virus Al

Virus: Influenza A, RSV, ADV3, HSV-II were purchased from Chinese Academy of Preventive Medical Science.

Control drug: Moroxydine hydrochloride tablet, batch number: 950715–2.

Cytotoxicity test: The test drug and the positive control drug were respectively diluted into the solution of 1%, 5%, 10%, 15% and 20% with the cell maintenance media. Take the diluent with the concentration of 0.6%–12% and put them into the test tubes lined with monolayer cell. Every percentage of the diluent was inoculated to four tubes. The inoculating tubes were observed at 35° C. for 5–7 days. The result showed that the development of cells lined in the tube was well at the range of concentration from 1% to 20% of the drug products, both tablet and granule. The result illustrated that the drug products, both tablet and granule had no toxicity for the cells at the range of concentration.

Dosage of inoculation: Every kind of virus was diluted into a titer of $1000TCD_{50}/0.1$ ml with cell maintenance media. The amount of 0.1 ml of the dilution was inoculated into each tube with the monolayer Holn cells at 37° C. The diluent was absorbed for 2 hours.

Method

Inhibitory effect of the drug product for virus was observed with the method of Cytopathic Effect (CPE). According to the result of viral toxicity test, the titer of the virus was $1000TCD_{50}/0.1$ ml. The four kinds of virus above-mentioned were respectively diluted into a titer of $1000TCD_{50}/0.1$ ml with the cell maintenance media. The influenza virus included four blood-clotting units and separately infected the cell tubes in the five groups. Each group comprised four tubes. The 0.1 ml of virus diluent in each tube was absorbed at 37° C. for 2 hours. Add the diluent of the drug product to the cell tubes with 1%, 5%, 10%, 15% and 20% of concentration respectively. Culture the diluents at 35° C. and observed them for 5–7 days, while controlled the drug toxicity with the virus control group and set up the blank control group.

Result

In the test of anti-virus effect of the drug product in vitro, The four kinds of virus replication in the cells can be completely inhibited at 50 mg/ml of concentration of the drug product. The result showed that the test drug had inhibitory effect for the virus in vitro. The test indicates that drug product is a kind of new dosage form of Traditional Chinese Medicine with a wide inhibitory effect for the virus proliferation, and the effect is better than Moroxydine hydrochloride tablet, as a control drug. The result is showed in the Table 19.

TABLE 19

Inhibitory Effect of the drug product for the virus

| Test Drug | Percentage (%) | Concentration (mg/ml) | Influenza | RSV | ADV3 | HSV-II |
|---|---|---|---|---|---|---|
| Diantic Tablet | 1 | 10 | − | + | − | − |
| | 5 | 50 | − | − | − | − |
| | 10 | 100 | − | − | − | − |
| | 15 | 150 | − | − | − | − |
| | 20 | 200 | − | − | − | − |
| Moroxydine hydrochloride | 1 | 10 | + | + | + | + |
| | 5 | 50 | − | + | + | + |
| | 10 | 100 | − | + | + | + |
| | 15 | 150 | − | + | + | + |
| | 20 | 200 | − | + | + | + |

Note:
"−": Virus proliferation was inhibited and no pathologic change was found in the cells.
"+": The cell had pathologic change.

4. Effect of the Drug Product for the Mice with Influenza Al

Material

Virus: The influenza virus purchased from Chinese Academy of Preventive Medical Science.

Animal: The Kunming mice provided by Institute of Materia Medica, Chinese Academy of Medical Science. The number of Quality Certificate is 01-3001.

Method

The mice were randomly divided into three groups. The equal number of 100 mice was used for the virus control group, the test group and the drug control group. A total of 0.03 ml of influenza Al with $10^{-2}$(?) of titer was inoculated to the each of mice. The test drug was immediately given after intranasal vaccination. A total of 0.4 ml/20 mg of the drug product (contain 7.5 g/kg of raw material) was given for the drug control group with virus and drug control group (virus free). The test drug was given again after a period of 6 hours of administration. And then, the test drug was given one time everyday for 9 days. The test was observed for a period of 10 days and recorded for many times everyday, including the time of death of mice each. The result showed that the mortality of infected mice with influenza Al had significantly difference (P<0.01) between the test group, the drug control group and the virus control group. It indicated that the drug product of Flos Lonicerae, Fructus Forsythiae and Radix Scutellariae had greater protective effect for the infected mice with the influenza virus. The result was showed in the Table 20.

TABLE 20

Inhibitory effect of the drug product for the influenza virus A1

| Group | Cases | Survival No. | Death No. | Death rate (%) | P |
|---|---|---|---|---|---|
| Blank | 100 | 5 | 95 | 85 | |
| Test drug | 100 | 10 | 81 | 81 | <0.01 |

Note:
Blank control: the virus control group which only contains virus.

TABLE 21

Effect of the drug product on xylene-induced inflammation in the ears of mice

| Group | Dosage (g/kg) | No. of mice | Post-test Weight of Ear (mg, X ± SD) | P Value |
|---|---|---|---|---|
| Blank | — | 10 | 5.63 ± 2.24 | |
| Test 1 | 1.44 | 10 | 4.37 ± 1.80 | <0.05 |
| Test 2 | 0.75 | 10 | 4.02 ± 1.50 | <0.05 |

Note:
Test group 1 or test group 2 was given different dosage of the sample of drug product produced with new techniques.

6. Effect of the Drug Product on Swelling Toes in Rats

A group of 50 rats with an equal number of male and female (weight of 180–250 g) were randomly divided into five groups. The volume of toes were measured and used for the normal value. The drug product of Flos Lonicerae, Fructus Forsythiae and Radix Scutellariae had a concentration of 1.44 g/kg or 0.72 g/kg in the experimental groups, and 10 ml/kg of the equivalent NS was given to the control group. 0.1 ml of 10% fresh albumen was injected into the toes of hind limbs to produce inflammation. The swelling degree of toes was measured for 0.5 hr, 1 hr, 2 hrs and 4 hrs after the administration. The result in the test groups showed that the drug product had an evident inhibition for the albumen-induced swelling toes for four consecutive hours (Table 22). The result indicated that the drug product had a powerful inhibition on the inflammation.

TABLE 22

Effect of the drug product on swelling toes in rats

| Group | Dose (g/kg) | No | Swelling (ml, X ± SD) | | | | |
|---|---|---|---|---|---|---|---|
| | | | 0.5 h | 1 h | 2 h | 3 h | 4 h |
| Blank | — | 10 | 0.63 ± 0.18 | 0.66 ± 0.17 | 0.57 ± 0.16 | 0.52 ± 0.16 | 0.37 ± 0.03 |
| Test 1 | 1.44 | 10 | 0.51 ± 0.17 | 0.45 ± 0.14** | 0.40 ± 0.12* | 0.37 ± 0.02* | 0.21 ± 0.06* |
| Test 2 | 0.72 | 10 | 0.53 ± 0.19 | 0.48 ± 0.16* | 0.44 ± 0.10* | 0.41 ± 0.09* | 0.27 ± 0.07 |

Note:

*P < 0.05, **P < 0.01, compared with the control group.

Test group 1 or test group 2 was given different dosage of the sample of drug product produced with new techniques.

5. Effect of the Drug Product for Xylene-Induced Inflammation in the Ears of Mice A total of 40 common male mice (18–20 g) were divided into four groups. They were administered the sample drug products (1.44 g/kg, 0.72 g/kg) in the test groups, or were given the equivalent NS (0.5 ml/20 g). The 0.03 ml of xylene was injected into the left ear of mice in order to cause inflammation for at least 3 hours. The mice were later killed and the ears were weighed. The swelling degree indicated a difference in weight between the normal ear and the inflammatory one. The results showed that the drug product of Flos Lonicerae, Fructus Forsythiae and Radix Scutellariae had a significant inhibition for xylene-induced inflammation in mice's ear. (Table 21)

7. Effect of the Drug Product for Artificial Pyrexy in Rabbit

A total of 50 rabbits with an equal number of male and female (weight of 2.0–3.0 kg) were randomly divided into five groups. The normal temperature of each rabbit was measured twice within an interval of 30 minutes. The drug products were given with 1.0 g/kg or 0.5 g/kg of concentration and 2 ml/kg of volume of water. Typhoparatyphoid A and B vaccine was injected into the auricle vein with 1 ml/kg of concentration. The rectal temperature was taken four times within an interval of one hour and the data was recorded from 0–4 hours after the injection. The rectal temperature was compared between the groups. The result of the test indicated that the drug product of Flos Lonicerae, Fructus Forsythiae and Radix Scutellariae was effective for pyretolysis in rabbits and became effective within 2 hours post-administration. The remission for artificial pyrexy can last over four hours. (Table 23)

TABLE 23

Effect of the drug product for artificial pyrexy in rabbit

| Group | Dose (g/kg) | Normal Temperature | Mean Difference of post-test (° C., X ± SD) | | | |
|---|---|---|---|---|---|---|
| | | | 1 h | 2 h | 3 h | 4 h |
| Blank | — | 38.94 ± 0.30 | 0.90 ± 0.36 | 1.16 ± 0.32 | 0.83 ± 0.30 | 0.51 ± 0.23 |
| Test 1 | 1 | 38.77 ± 0.37 | 0.82 ± 0.25 | 0.61 ± 0.24** | 0.47 ± 0.11** | 0.23 ± 0.11** |
| Test 2 | 0.5 | 38.75 ± 0.20 | 0.87 ± 0.20 | 0.82 ± 0.21** | 0.57 ± 0.24* | 0.26 ± 0.20* |

Note:
*$P < 0.05$, **$P < 0.01$, compared with the control group
Test group 1 or test group 2 was given different dosage of the sample of drug product produced with new techniques.

Example 4
Methodology Study on the Quality Control Standards of the Drug Product This invention provides a method of High Performance Liquid Chromatography and Finger Printing Spectrum (HPLC-FPS) and a systematic quality analysis for the detection and control of the extracts and drug product of Fructus Forsythiae, Flos Lonicerae and Radix Scutellariae.

This invention provides a method for identifying with HPLC-FPS the composition of raw materials of Flos Lonicerae, Fructus Forsythiae and Radix Scutellariae respectively, wherein the composition comprises Chlorogenic acid, Phillyrin, and Baicalin.

This invention provides a method for determining with High Performance Liquid Chromatography (HPLC) and calculating with two-point revise method the content of Chlorogenic acid, Phillyrin, Baicalin from the raw materials of Flos Lonicerae, Fructus Forsythiae and Radix Scutellariae respectively.

This invention provides a method for identifying with HPLC-FPS the composition of water extracts of Flos Lonicerae and Fructus Forsythiae respectively, wherein the said composition further comprises Chlorogenic acid, Phillyrin.

This invention provides a method for identifying with HPLC-FPS the composition of water extract of Radix Scutellariae, wherein the said composition comprises Baicalin.

This invention provides a method for determining with HPLC and calculating with two-point revise method the content of Chlorogenic acid from the water extracts of Flos Lonicerae and Fructus Forsythiae.

This invention provides a method for determining with HPLC and calculating with two-point revise method the content of Phillyrin from the water extracts of Flos Lonicerae and Fructus Forsythiae.

This invention provides a method for determining with HPLC and calculating with two-point revise method the content of Baicalin from the water extract of Radix Scutellariae.

This invention provides a method for identifying with Gas Chromatogram (GC) the main ingredients and their content of the supercritical extracts of Flos Lonicerae and Fructus Forsythiae, wherein the ingredients further comprise β-pinene, sabinene, α-pinene and linalool.

This invention provides a method for identifying and controlling with HPLC-FPS the composition of the drug product of Flos Lonicerae, Fructus Forsythiae and Radix Scutellariae, wherein said composition further comprises Chlorogenic acid, Phillyrin, Baicalin, Caffeic acid and Baicalein.

This invention provides a method for determining with HPLC and calculating with two-point revise method the content of the drug product composition of Flos Lonicerae, Fructus Forsythiae and Radix Scutellariae respectively, wherein the said the content of the composition further comprises Chlorogenic acid, Phillyrin and Baicalin.

This invention provides a method as the above-mentioned for determining the content of the drug product composition of Flos Lonicerae, Fructus Forsythiae and Radix Scutellariae. The range of content respectively is: 1.05%–1.68% for Chlorogenic acid, 0.10%–0.40% for Phillyrin, 8.71%–14.80% for Baicalin.

This invention provides a method for controlling with a 210 nm–400 nm wavelength of Photodiode Array Detector (PAD) the HPLC-FPS peaks of the composition from of Flos Lonicerae, Fructus Forsythiae and Radix Scutellariae. Wherein the said composition further comprise Chlorogenic acid, Phillyrin, Baicalin, Caffeic acid and Baicalein.

This invention provides a method for determining with HPLC-FPS the composition of raw materials and drug product. Wherein the said method comprises the following steps: (1) Set up the chromatographic fingerprinting of Flos Lonicerae Fructus Forsythiae and Radix Scutellariae from raw materials; (2) Determine the certified characteristic/comparable peaks of Flos Lonicerae, Fructus Forsythiae and Radix Scutellariae respectively, in accordance with their relative retention of chromatographic peaks; (3) Compare and determine the peaks of undetermined ingredients with the characteristic/comparable peaks.

Detailed Studies of Quality Control of the Drug Product
1. Standards of Raw Medical Materials Flos Lonicerae (dry bud of *Lonicera japonica* Thumb) is mainly produced in Henan and Shandong. The product must be in accordance to the related provisions of the item of Flos Lonicerae listed on Page 177 in Chinese Pharmacopoeia (2000 Edition, Part I).

Fructus Forsythiae is the dry fruit of *Forsythia suspensa* (Thumb) Vahl. Its main producing areas are Shanxi and Henan. The product must be in accordance to the related provisions of the item of forsythia listed on Page 135 in Chinese Pharmacopoeia (2000 Edition, Part I).

Radix Scutellariae is the dry root of *Scutellaria baicalensis* Georgi. Its main producing areas are the provinces of Hebei, Heilongjiang and Neimenggu. The product must be in accordance to the related provisions of the item of Radix Scutellariae listed on Page 248 in Chinese Pharmacopoeia (2000 Edition, Part I).

Content Determination

1) Content Determination for Chlorogenic Acid of Flos Lonicerae Material.

a) Apparatus and Material i) Apparatus:

Chromatographic Working Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory.

ii) Sample:

Standard sample: Chlorogenic acid. Purchased from the Drug and Biology Product Test Agency.

Sample: Flos Lonicerae (provided by Shanghai Huayu pharmaceutical Co. Identified by Shanghai Chinese Medicine Quality Control Supervision and Testing Station as dried buds of Lonicera japonica Thumb mainly produced in Shandong and Henan.

Regents: methanol (HPLC), re-distilled water, anhydrous acetic acid (analysis pureness).

b) Chromatographic Condition

Chromatographic Column: Inertsil ODS-3,5 $\mu$m, 4.6 mm*250 mm (made in Japan). Protection Column: phenomenex C18 (ODS), 4 mmL*3.0 mmID. Floating Phase: the proportion of methanol to water (contains 2% acetic acid) is in a ratio of about 25 to 75. Velocity of flow: 1 ml/min. Testing Wavelength: 280 nm. Column Temperature: room temperature.

c) Standard Curve

Preparation of Standard Solution: a certain amount of Chlorogenic acid dried using diphosphorus pentaoxide for 48 hrs was weighed and used as the comparing solution. Isolate it with methanol/water (1:1)(V/V). Prepare 0.5 mg/ml of concentration.

Take the standard solution and inject a sample of 2.5, 5, 10, 15 and 20 ul under Chromatographic Condition and record the sample volume and the peak areas. Calculate the following regression equation:

$A=450580+3941609.92C$; $r=0.9992$; Linear Range: 1.25 ug–10 ug.

d) Preparation of the Sample Solution:

Take some Flos Lonicerae, rub it into the powder and pass the 40 item of bolt. Weigh exactly 134 mg of powder and put it into the centrifuge tube. Add 4 ml of methanol/water to a mixer and mix them for 1 minute, and then ultrasonically vibrate and extract for 1 minute.

Take the upper clear solution, add 4 ml of methanol/water to the residue and treat the solution for 15 min under ultrasonic wave. Centrifuge and take the upper clear solution. Wash the residue with 1.5 ml of methanol/water and mix the cleaning solution with the upper clear solution. Scale the volume of sample solution in a 10 ml of flask and filter with 0.45 um of filtration before giving sample.

Take the sample solution under the chromatographic condition to have HPLC analysis. Calculate the ingredient content of the sample according to the two-point revise method. The formula is given as follows:

$CX=C1+(C2-C1)*(AX-A1)/(A2-A1)$

C1 and C2 stand for the quantities of the standard respectively.

A1 and A2 stand for the peak areas of the standard respectively.

CX and AX stand for the quantity and peak area of the sample.

d) Content Determination Results:

The content of chlorogenic acid of Flos Lonicerae is about 1.05%–1.68%.

2) Content Determination for Phillyrin of Fructus Forsythiae Material.

a) Apparatus and Material i) Apparatus:

Chromatographic Working Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory.

ii) Samples:

Standard sample: Phillyrin, purchased from China drug and biological product testing agency.

Sample: Fructus Forsythiae from Chinese traditional medicine (provided by Shanghai HuaYu Pharmaceutical Co. Identified by Shanghai Supervise Agency of quality in the Chinese traditional medicine as dry fruits of *Forsythia suspensa* (Thumb) Vahl which are mainly produced in Henan and Shanxi.

b) Chromatographic Condition

Chromatographic column: Inertsil ODS-3,5 $\mu$m, 4.6 mm*250 mm (Made in Japan). Protection column: phenomenex C18 (ODS), 4 mmI*3.0 mmID. Floating phase: the proportion of acetonitrile and water is in a ratio of about 28 to 72.

Velocity of flow: 1 ml/min. Detection of wavelength: 280 nm.

Temperature of column: room temperature.

c) Standard Curve

Preparation of Standard Solution:

Weigh a certain ammount of phillyrin dried with $P_2O_5$ for 48 hr as comparison, isolate it with methanol/water (1:1 v/v) and prepare a solution with 0.5 mg/ml of concentration.

Take the standard solution under the above chromatographic condition. Inject the sample solution of 2.5 ul, 5 ul, 10 ul, and 20 ul respectively and record the peak areas and the sample volume. Calculate the regression equation:

$A=51826+1897520.24C$, $r=0.9998$, Linear range: 1.25 ug–10 ug.

d) Sample Determination

Preparation of the Sample Solution:

Take some material of Fructus Forsythiae and rub it into powder and then pass the 40 item of bolt. Weigh exactly 1.072 g of the powder and put it into the centrifuge tube. Add 4 ml of methanol/water to a mixer and mix them for 1 minute, and then ultrasonically vibrate and extract for 15 min. Centrifuge and take the upper clear solution. Washing the residue with 1.5 ml of methanol/water and mixing the cleaning solution with the upper clear solution. Scaling the volume of sample solution in a 10 ml of flask. Filtering the solution with 0.45 um of filtration membrane before giving sample.

Take the above sample solution under the chromatographic condition to have HPLC analysis. Calculate the ingredient content of the sample according to the two-point revise method. The formula is given as follows:

$CX=C1+(C2-C1)*(AX-A1)/(A2-A1)$

C1 and C2 stand for the quantities of the standard respectively.

A1 and A2 stand for the peak areas of the standard respectively.

CX and AX stand for the quantity and peak area of the sample.

e) The Results of Determination:
The content of Phillyrin of Fructus Forsythiae is about 0.10%–0.40%.

3) Content Determination of Baicalin of Radix Scutellariae Material a) Apparatus and Material
i) Apparatus:
Chromatographic Work Station: Perkin ELMER 1022 LC Plus. Pump: Perkin ELMER series 200 LC pump. Detector: PERKIN ELMER DAD 235C. Volution mixer: Shanghai Medical University Apparatus Factory; centrifuge and deposition machine; Shanghai operation instruments factory. Bath boiler: Jangsu Changhsu Medical Instrument Factory.

ii) Samples:
Standard sample: Baicalin purchased from China Drug and Biology Product Test Agency.
Sample: Radix Scutellariae (provided by Shanghai Huayu Medical Co. and identified as dried roots of *Scutellaria baicalensis* Georgi plant which are mainly produced in Shandong and Hebei by Shanghai Traditional Medicine Quality Supervise & Test agency;
Regents: Methanol (HPLC), distilled water and glacial acetic acid (analytical pureness)

b) Chromatographic Condition
Chromatographic Column: Inertsil ODS-3,5 μm, 4.6 mm*250 mm (made in Japan). Protection Column: phenomenex C18 (ODS), 4 mmI*3.0 mmID. Floating Phase: the proportion of methanol and water (contain 2% caetic acid) is in a ratio of about 65 to 35. Velocity of flow: 1 ml/min. Detection Wavelength: 280 nm. Temperature of column: room temperature.

c) Standard Curve
Preparation of Standard Solution:
Weigh exactly a certain amount of baicalin dried with $P_2O_5$ for 48 hrs as comparing solution, and isolate it with methanol/water (1:1 v/v). Prepare the solution to 0.1 mg/ml of concentration.
Take standard solution under the chromatographic condition and inject the sample of 2.5 ul, 5 ul, 10 ul, 20 ul respectively. Record the peak areas and the sample volume, and calculate the regression equation:

$A = -308002 + 14174938.4C$; $r = 0.9993$; Linear range: 0.25 ug–2 ug d) Sample Determination
Preparation of the Sample Solution:
Take some material of Radix Scutellariae, rub it into powder, and pass the 40 item of bolt. Weigh exactly 100 mg of powder and put it to the centrifuge tube. Add 20 ml solution of methanol/water to a mixer and mix them for 15 minute, then ultrasonically vibrate and extract for 15 minute. Centrifuge and take the upper clear solution. Wash the residue with 5 ml of methanol/water and combine it with the upper clear solution. Scale the volume of sample solution in a 50 ml of flask. Filter it with 0.45 um of filtration membrane before giving samples.
Take the above sample solution under the Chromatographic Condition to have HPLC analysis. Calculate the ingredient content of the sample according to the two-point revise method. The formula is given as follows:

$CX = C1 + (C2-C1)*(AX-A1)/(A2-A1)$

C1 and C2 stand for the quantities of the standard respectively.
A1 and A2 stand for the peak areas of the standard respectively.
CX and AX stand for the quantities and peak area of the sample.

e) The Results of Determination
The content of Baicalin in Radix Scutellariae is about 3.01%–4.47%.

Fingerprint Chromatography of Raw Materials

1) Fingerprint Chromatography of Flos Lonicerae
a) Instrument and Material
i) Instrument: Waters 510 HPLC Pump (American). Waters TM 996 PDA Photodiode Array Detector Waters pump Control Module. Chromatography Working Station: Millenium 32, Pentum III, UV wave, Swirlly mixer: XW-80A; Centrifugal precipitator: 80–1.
ii) Regent: Acetonitrile (HPLC) purchased by Shanghai Xingshi Biological Engineering Co. LTD; Methol (HPLC) purchased by Shanghai chemical regent Co.; Glacial acetic acid and Sparklin pure distilled water.
iii) Standard product: Chlorogenic acid, sold by China Test Institute of medical and biological product
iV) Samples: Flos Lonicerar of raw Material produced in Shandong, sold by Shanghai Huayu Pharmaceutical co. Testified to the dry bud of Lonicera Japonica Thumb by Shanghai Quality test station of TCM.

b) Chromatographic Condition
Chromatographic Column: Inertsil ODS-3,5 μm, 4.6 mm*250 mm (made in Japan). Protecting Column: phenomenex C18 (ODS), 4 mm*3.0 mmID. Floating Phase: acetonitrile: 1% acetic acid solution (V/V). Temperature: room temperature (air-condition in room is between 18~22° C.); Inspector: Inspector of PDA, 210~400 nm whole wavelength scan.

c) Preparation of Sample Solution
Take some material of Flos Lonicerae, rub it into powder and pass the 40 item of bolt. Weigh exactly 187.5 mg of the powder and put it into the centrifuge tube. Add 4 ml of methanol/water to a mixer and mix them for 1 min, and ultrasonically vibrate and extract it for 15 min. Centrifuge and take the upper solution. Wash the residue with 1.5 ml of methanol/water and combine it with the upper clear solution. Scale the volume of sample solution in a 10 ml of flask, and filter it with 0.45 um of filtration membrane before giving sample.

d) Fingerprint Chromatogram of Chlorogenic Acid of Flos Lonicerae Material (HPLC-FPS)
Take the above sample solution under the Chromatographic Condition to have HPLC analysis. The result is given in Table 19. The number of the HPLC-FPS peak is about 8 at low limit and 11 at high limit, when the peak area of the HPLC-FPS is about $2.0 \times 10^6$ and over. The $3^{rd}$ peak of the HPLC-FPS is known as the characteristic peak of Chlorogenic acid. The condition of characteristic peak of Chlorogenic acid was limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 2.

TABLE 19

Peak Results of Flos Lonicerae Raw Material

| Peak No. | RT | Area | Height | Amount | Units |
|---|---|---|---|---|---|
| Peak 1 | 6.342 | 493957 | 30721 | | |
| Peak 2 | 6.673 | 466284 | 20726 | | |
| Peak 3 | 8.702 | 9085333 | 708461 | | |
| Peak 4 | 9.261 | 514788 | 21747 | | |
| Peak 5 | 15.580 | 358760 | 20142 | | |
| Peak 6 | 18.533 | 4871688 | 374813 | | |
| Peak 7 | 19.519 | 1121040 | 75033 | | |

TABLE 19-continued

Peak Results of Flos Lonicerae Raw Material

| Peak No. | RT | Area | Height | Amount | Units |
|---|---|---|---|---|---|
| Peak 8 | 20.059 | 301004 | 10437 | | |
| Peak 9 | 22.437 | 357890 | 29941 | | |
| Peak 10 | 27.075 | 762326 | 22938 | | |
| Peak 11 | 27.566 | 931937 | 21034 | | |

2) Fingerprint Chromatogram of Material Fructus Forsythiae a) Apparatus and Material i) Instrument: Waters 510 HPLC Pump (American), Waters TM 996 PDA Photodiode Array Detector Waters pump Control Module. Chromatography Working Station: Millenium 32, Pentum III, UV wave. Swirlly mixer: XW-80A. Centrifugal precipitator: 80–1.

ii) Regent: Acetonitrile (HPLC) purchased by Shanghai Xingshi Biological Engineering Co., LTD. Methol (HPLC) purchased by Shanghai chemical regent Co. Glacial acetic acid and Sparklin pure distilled water.

iii) Standard product: Phillyrin purchased from Drug and Biological Product Testing Agency of China.

iv) Sample: Fructus Forsythiae of the Chinese medicine (provided by Shanghai Huayu Pharmaceutical Co. and testified to be the dry fruits of Forsythia suspensa (Thumb) Vahl produced in Henan and Shanxi.

b) Chromatographic Condition

Chromatographic Column: Inertsil ODS-3,5 μm, 4.6 mm*250 mm (made in Japan). Protecting Column: phenomenex C18 (ODS), 4 mm*3.0 mmID. Floating Phase: acetonitrile: 1% acetic acid solution (V/V). Temperature: room temperature (air-condition in room is between 18–22° C.). Inspector: Inspector of PDA, 210–400 nm whole wavelength scan.

c) Sample Solution Preparation:

Take some material of fructus forsthiae and rub it into powder, and pass 40 item of bolt. Weigh exactly 375 mg of the powder and put it into the centrifuge tube. Add 4 ml of methanol/water to a mixer and mix them for 1 min, then ultrasonically vibrate and extract for 15 min. Centrifuge and take the upper clear solution. Wash the residue with 1.5 ml of methanol/water and combine it with the upper clear solution. Scale the volume of sample solution in a 10 ml of flask, and filter it with 0.45 um of filtration membrane before giving sample.

d) Fingerprint Chromatogram of Fructus Forsythiae Raw Material (HPLC-FPS)

Take the above sample solution under the Chromatographic Condition to have HPLC analysis. The result is given in Table 20. The number of the HPLC-FPS peak is about 11 at low limit and 14 at high limit. The peak area of the HPLC-FPS is about 2.0×10$^6$ and over. The 8$^{th}$ peak of the HPLC-FPS is known as the characteristic peak of Phillyrin. The condition of characteristic peak of Phillyrin was limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 3.

TABLE 20

Peak Results of Fructus Fosythiae Raw Material

| Peak No. | RT | Area | Height | Amount | Units |
|---|---|---|---|---|---|
| Peak 1 | 10.258 | 814090 | 48518 | | |
| Peak 3 | 13.135 | 626570 | 42575 | | |

TABLE 20-continued

Peak Results of Fructus Fosythiae Raw Material

| Peak No. | RT | Area | Height | Amount | Units |
|---|---|---|---|---|---|
| Peak 4 | 13.525 | 6745808 | 645897 | | |
| Peak 5 | 14.163 | 589315 | 42302 | | |
| Peak 6 | 14.573 | 517509 | 21032 | | |
| Peak 7 | 19.890 | 621807 | 25787 | | |
| Peak 8 | 20.778 | 586221 | 44436 | | |
| Peak 9 | 22.385 | 4736969 | 432780 | | |
| Peak 10 | 24.774 | 706135 | 56201 | | |
| Peak 11 | 26.242 | 692217 | 47573 | | |
| Peak 12 | 27.217 | 1445507 | 35586 | | |
| Peak 13 | 27.946 | 588955 | 17532 | | |
| Peak 14 | 30.779 | 655429 | 54190 | | |

3) Fingerprint Chromatogram of Radix Scutellariae Raw Material a) Apparatus and Material i) Instrument: Waters 510 HPLC Pump (American), Waters TM 996 PDA Photodiode Array Detector Waters pump Control Module. Chromatography Working Station: Millenium 32, Pentum III, UV wave. Swirlly mixer: XW-80A. Centrifugal precipitator: 80–1.

ii) Regent: Acetonitrile (HPLC), purchased by Shanghai Xingshi Biological Engineering Co., LTD. Methol (HPLC) purchased by Shanghai chemical regent Co. Glacial acetic acid and Sparklin pure distilled water.

iii) Standard product: Baicalin purchased from Drug and Biological Product Testing Agency of China.

iv) Sample: Radix Scutellariae of the Chinese medicine (provided bby Shanghai Huayu Pharmaceutical Co. and testified to be the dry roots of Scutellaria baicalensis Georgi by The Chinese Medicine Quality Testing Station of Shanghai, which are mainly produced in Shandong and Hebei.

b) Chromatographic Condition

Chromatographic Column: Inertsil ODS-3, 5 μm, 4.6 mm*250 mm (made in Japan). Protecting Column: phenomenex C18 (ODS), 4 mm*3.0 mmID. Floating Phase: acetonitrile: 1% acetic acid solution (V/V). Temperature: room temperature (air-condition in room is between 18–22° C.). Inspector: Inspector of PDA, 210–400 nm whole wavelength scan.

c) Preparation of the Sample Solution

Take some material Radix Scutellariae and rub it into powder, and pass 40 item of bolt. Weigh 187 mg of the powder and put it into the centrifuge tube. Add 4 ml of methanol/water into a mixer and mix them for 1 min, then ultrasonically vibrate for 15 min. Centrifuge and take the upper clear solution, and wash the residue with 1.5 ml of methanol/water. Combine the sample solution with the upper clear solution. Scale the volume of sample solution in a 10 ml of flask, and filter it with 0.45 um of filtration membrane before giving sample.

d) Fingerprint Chromatogram of Raw Material Radix Scutellariae (HPLC-FPS)

Take the above sample solution the Chromatographic Condition to have HPLC analysis. The result is given in Table 21. The number of the HPLC-FPS peak is about 22 at low limit and 25 at high limit. The peak area of the HPLC-FPS is about 2.0×10$^6$ and over. The 12$^{th}$ peak of the HPLC-FPS is known as the characteristic peak of Baicalin and the 20$^{th}$ peak of HPLC-FPS is known as the peak of Baicalein. The conditions of characteristic peak of Baicalin and Baicalein were limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 4.

TABLE 21

Peak Results of Radix Scutellariae Raw Material

| Peak No. | RT | Area | Height | Amount | Units |
|---|---|---|---|---|---|
| Peak 1 | 14.959 | 2237919 | 227173 | | |
| Peak 2 | 15.816 | 795422 | 77122 | | |
| Peak 3 | 16.109 | 1368881 | 150941 | | |
| Peak 4 | 16.599 | 458822 | 49718 | | |
| Peak 5 | 16.912 | 1857671 | 129863 | | |
| Peak 6 | 19.305 | 1540200 | 98209 | | |
| Peak 7 | 20.148 | 418214 | 20489 | | |
| Peak 8 | 21.039 | 1760153 | 142473 | | |
| Peak 9 | 22.232 | 333048 | 37812 | | |
| Peak 10 | 22.382 | 719683 | 48417 | | |
| Peak 11 | 23.289 | 878561 | 77954 | | |
| Peak 12 | 23.582 | 63908461 | 2742950 | | |
| Peak 13 | 24.760 | 324362 | 18757 | | |
| Peak 14 | 25.143 | 684277 | 47331 | | |
| Peak 15 | 25.756 | 441537 | 31207 | | |
| Peak 16 | 26.414 | 6035150 | 505894 | | |
| Peak 17 | 26.688 | 7422217 | 356766 | | |
| Peak 18 | 27.544 | 505176 | 42508 | | |
| Peak 19 | 27.902 | 15993786 | 932298 | | |
| Peak 20 | 30.030 | 3697771 | 324366 | | |
| Peak 21 | 36.365 | 2645077 | 228485 | | |
| Peak 22 | 36.712 | 729275 | 46343 | | |
| Peak 23 | 37.711 | 1377723 | 100271 | | |

2. Quality Standard of Intermediate

The extract powder of Flos Lonicerae and Fructus Forsythiae was obtained with $CO_2$ supercritical extraction and sub-boiling aqueous extraction successively. The extract of Radix Scutellariae was finely obtained with water extraction.

Content Determination

1) Content Determination of Chlorogenic Acid of Flos Lonicerae and Fructus Forsythiae extracts.

a) Apparatus and Material i) Apparatus:

Chromatographic Work Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory ii) Sample:

Extracts of Flos Lonicerae and Fructus Forsythiae (provided by National Engineering Research Center of Traditional Medicine)

b) Chromatographic Condition

Chromatographic Column: Inertsil ODS-3,5 um, 4.6*250 mm (made in Japan). Protecting Column: phenoemenex C18 (ODS), 4 mml*3.0 mmID. Floating Phase: methanol: water (contains 2% acetic acid)=25:75

Velocity of flow: 1 ml/min. Testing wavelength: 280 nm.

Temperature of column: room temperature.

c) Standard Curve

Preparation of Standard Solution:

Weigh exactly certain ammount of phillyrin dried with $P_2O_5$ for 48 hr as comparison. Isolate it with methanol/water (1:1 v/v) and prepare it into a sample solution with 0.1 mg/ml of concentration. Take standard solution under the above chromatographic condition. Inject the sample solution of 2.5 ul, 5 ul, 10 ul, 20 ul, respectively and record the peak areas and the sample volume. Calculate the regression equation:

$A=450580+3941609.92C$, $r=0.9992$, Linear range: 1.25 ug–10 ug.

d) Determination of the Sample:

Preparation of the Sample Solution:

Take the powder of Flos Lonicerae and Fructus Forsythiae extracts. Weigh exactly 170.5 mg of the powder and put into the centrifuge tube. Add 4 ml of methanol/water into a mixer and mix them for 1 min, then ultrasonically vibrate and extract for 15 min. Centrifuge and take the upper clear solution. Add 4 ml of methanol/water solution to the residue and treat it under ultrasonic waves for 15 min. Centrifuge and take the upper clear solution. Wash the residue with 1.5 ml of methanol/water and combine it with the upper clear solution. Scale the volume of the sample solution in a 10 ml of flask and filter the solution with the 0.45 um of filtration membrane before giving sample.

Take the above sample solution under the Chromatographic Condition to have HPLC analysis. Calculate the ingredient content of the sample according to the two-point revise method. The formula is given as follows:

$$Cx=C1+(C2-C1)*(Ax-A1)/(A2-A1)$$

C1 and C2 stand for the qualities of the standard sample respectively.

A1 and A2 stand for the peak areas of the standard sample respectively.

Cx and Ax stand for the quality and the peak area of the sample.

e) Examples of the Content Determination

Example 1

Take the Extract of Flos Lonicerae and Fructus Forsythiae and Determine the Content of Chlorogenic Acid with the above method. The result is 2.52%.

Example 2

Take the extracts of Flos Lonicerae and Fructus Forsythiae and determine the content of Chlorogenic Acid with the above method. The result is 2.93%.

Example 3

Take the extractors of Flos Lonicerae and Fructus Forsythiae and determine the content of Chlorogenic Acid with the above method. The result is 2.15%.

The result of the content is about: 1.00%–3.30%.

2) Content Determination of Phillyrin of Flos Lonicerae and Fructus Forsythiae extracts a) Apparatus and Material i) Apparatus:

Chromatographic Work Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory.

ii) Sample:

Extracts of Flos Lonicerae and Fructus Forsythiae (provided by National Engineering Research Center of Traditional Medicine)

b) Chromatographic Condition

Chromatographic Column: Inertsil ODS-3,5 um, 4.6 mm*250 mm (made in Japan). Protecting Column: phenomenex C18 (ODS), 4 mm*3.0 mmID. Floating Phase: acetonitrile: water=28:72. Velocity of flow: 1 ml/min. Testing wavelength: 280 nm. Column Temperature: room temperature.

c) Standard Curve

Preparation of Standard Solution:

Weigh exactly a certain ammount of phillyrin dried with $P_2O_5$ for 48 hrs to use it as the comparison solution. Dissolve with methanol/water (1:1 v/v) and prepare it into a solution with 0.5 mg/ml of concentration.

Take the standard solution under the above chromatographic condition. Inject the sample solution of 2.5 ul, 5 ul, 10 ul, 20 ul, respectively and record the peak areas and sample volume. Calculate the regression equation:

$$A=51826+1897520.24C,\ r=0.9998,\ \text{Linear range: } 1.25\ ug\text{--}10\ ug.$$

d) Determination of the Sample

Preparation of the Sample Solution:

Take the powder of Flos Lonicerae and Fructus Forsythiae extracts. Weigh exactly 292 mg of the powder and put it into the centrifuge tube. Add 4 ml of methanol/water into a mixer and mixing them for 1 min, then ultrasonically vibrate it for 15 min. Centrifuge and take the upper clear solution. Add 4 ml of methanol/water into the residue and treat it with ultrasonic waves for another 5 min. Centrifuge and take the upper clear solution. Wash the residue with 1.5 ml of methanol/water and combine the washings with the upper clear solution. Scale the volume of sample solution in a 10 ml of flask and filter the solution with 0.45 um of filtration membrane before giving sample.

Take the above sample solution under the Chromatographic Condition to have HPLC analysis. Calculate the ingredient content of the sample according to the two-point revise method. The formula is given as follows:

$$Cx=C1+(C2-C1)*(Ax-A1)/(A2-A1)$$

C1 and C2 stand for the qualities of the standard sample respectively.

A1 and A2 stand for the peak areas of the standard sample.

Cx and Ax stand for the quality and the peak area of the sample.

e) Content Determination:

Example 1

Take the extracts of Flos Lonicerae and Fructus Forsythiae and determine the content of Phillyrin with the above method. The result is 0.66%.

Example 2

Take the extracts of Flos Lonicerae and Fructus Forsythiae and determine the content of Phillyrin with the above method. The result is 0.59%.

Example 3

Take the extracts of Flos Lonicerae and Fructus Forsythiae and determine the content of Phillyrin with the above method. The result is 0.75%.

The result of the content is about: 0.2%–0.5%.

3) Content Determination of Baicalin of Radix Scutellariae Extracts a) Apparatus and Material i) Apparatus:

Chromatographic Work Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory ii) Sample: extracts of Radix Scutellariae (Provided by the Chinese Medicine Pharmaceutical and Technical Engineering Center of China)

b) Chromatographic Condition

Chromatographic Column: Inertsil ODS-3,5 um, 4.6 mm*250 mm (made in Japan). Protecting Column: Phenomenex C18 (ODS), 4 mm*3.0 mmID. Floating Phase: Methanol: Water (contain 2% acetic acid)=65:35. Velocity of flow: 1 ml/min. Testing wavelength: 280 nm. Column temperature: room temperature.

c) Standard Curve

Preparation of Standard Solution:

Weigh a certain amount of Baicatin previously dried with $P_2O_5$ for 48 hrs in order to be used as the comparing solution. Isolate it with methanol/water (1:1 v/v). Prepare a solution with 0.1 mg/ml of concentration.

Take standard solution under the chromatographic condition and inject a sample of 2.5 ul, 5 ul, 10 ul, and 20 ul respectively. Record the peak areas and the sample volume, and calculate the regression equation:

$$A=-308002+14174938.4C;\ r=0.9993;\ \text{Linear range: } 0.25\ ug\text{--}2\ ug.$$

d) Determination of the Sample

Preparation of the Sample Solution:

Take the extract of Radix Sutellariae and weigh exactly 10 mg of extract. Put it into a 100 ml of flask and add methanol/water. Ultrasonically vibrate and scale the volume in the flask. Filter the sample solution with 0.45 um of filtration membrane before injecting sample solution.

Take the above sample solution under the Chromatographic Condition to have HPLC analysis. Calculate the ingredient content of the sample according to the two-point revise method. The formula is given as follows:

$$Cx=C1+(C2-C1)*(Ax-A1)/(A2-A1)$$

C1 and C2: stand for the qualities of the standard sample respectively.

A1 and A2: stand for the peak areas of the standard sample respectively.

Cx and Ax: stand for the quality and the peak area of the sample.

e) Content Determination:

Example 1

Take the extracts of Radix Scutellariae and determine the content of Baicalin with the above method. The result is 93.4%.

Example 2

Take the extracts of Radix Scutellariae and determine the content of Baicalin with the above method. The result is 92.2%.

Example 3

Take the extracts of Radix Scutellariae and determine the content of Baicalin with the above method. The result is 91.3%.

The result of the content is about: 90.01%–93.40%.

4) Content Determination of the $CO_2$ Supercritical Extracts a) Material

The extracts of Flos Lonicerae and Fructus Forsythiae were extracted with the C02 Supercritical Fluid Extraction.

b) Apparatus

GC-9A Gas Chromatograph Chromatopac C-E1B data processing instrument (made in Japan).

c) Test Method
Gas Chromatographic Condition:
Use a SE-54 elastic quart chromatographic column with a 30-meter length and a 0.32 mm inner diameter. The temperature of gasification room is about 250° C. The column temperature ranges from 50–230° C., rising 4° C./min controlled by procedure. The carried gas is Nitrogen with pre-column pressure of 0.7 kg/cm. The column volume is 2 ml/min. The volume of injection is 0.4 ul. The detector is FID.

d) Qualitative Control

Example 1

Use the Gas Chromatography and contrast the sample with the standard solution. When the value of TR is about 8.551 min, β-pinene can be obtained. When the value of TR is about 12.926 min, linalool can be obtained. The absolute peak area is about 766933.

Example 2

Use the Gas Chromatography and contrast the sample with the standard solution. When the value of TR is about 8.575 min, β-pinene can be obtained. When the value of TR is about 12.919 min, linalool can be obtained. The absolute peak area is about 1138138.

Example 3

Use the Gas Chromatography and contrast the sample with the standard solution. When the value of TR is about 8.539 min, β-pinene can be obtained. When the value of TR is about 12.930 min, linalool can be obtained. The absolute peak area is about 906224.

e) GC-Chromatograph is Given in FIG. 8.

Fingerprint Chromatogram of Intermediate

1) Fingerprint Chromatogram of extracts of Flos Lonicerae and Fructus Fosythiae a) Apparatus and Material
Apparatus: as the above mentioned
Standard Sample: Chlorogenic acid and phillyrin are purchased from the Drug and Biological Product Testing Agency of China.
Sample: Extracts of Flos Lonicerae and Fructus Fosythia provided by National Engineering Research Center of Traditional Medicine.

b) Chromatographic Condition
Chromatographic Column: Inertsil ODS-3,5 um, 4.6 mm*250 mm (made in Japan). Protecting Column: phenomenex C18 (ODS), 4 mm*3.0 mmID. Floating Phase: acetonitrile, 1% acetic acid solution (V/V). Temperature: room temperature (air-condition in room is between 18~22° C.). Inspector: testing machine PDA, whole wavelength scan of 210~400 nm.

c) Preparation of the Sample Solution
Take the extracts of Flos Lonicerae and Fructus Fosythia and rub into powder. Then pass the 40 item of bolt. Weigh exactly 107.5 mg of the powder and put it into a centrifuge tube. Add 4 ml of methanol/water into a mixer and mix them for 1 min. Then ultrasonically vibrate it for 15 min. Centrifuge and take the upper clear solution. Add 4 ml of methanol/water into the residue and vibrate the solution under ultrasonic waves for another 15 min and then centrifuge it. Take the upper clear solution and wash the residue with 1.5 ml of methanol/water. Combine it with the upper clear solution and scale the sample solution in a 10 ml of flask. Filter the solution with the 0.45 um of filtration membrane before giving sample.

d) Fingerprint Chromatograph of the extracts of Flos Lonicerae and Fructus Fosythia.
Take the sample solution under the above Chromatographic Condition to have HPLC analysis. The result is given in the Table 22. The number of the HPLC-FPS peak is 18 at low limit and 23 at high limit. The peak area of the HPLC-FPS is about $2.0 \times 10^6$ and over. The $8^{th}$ peak of the HPLC-FPS is known as the characteristic peak of Chlorogenic acid, the $12^{th}$ peak of the HPLC-FPS is known as the characteristic peak of Caffeic acid and the $21^{st}$ peak of the HPLC-FPS is known as the characteristic peak of Phillyrin. The conditions of characteristic peaks of Chlorogenic acid, Caffeic acid and Phillyrin were limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 5.

TABLE 22

Peak results of the Extracts of Flos Lonicerae and Fructus Fosythia

| Peak No. | RT | Area | Height | Amount | Units |
| --- | --- | --- | --- | --- | --- |
| Peak 1 | 2.352 | 590936 | 105532 | | |
| Peak 2 | 2.821 | 345144 | 31096 | | |
| Peak 3 | 3.094 | 687602 | 80646 | | |
| Peak 4 | 3.918 | 320428 | 55429 | | |
| Peak 5 | 4.382 | 395834 | 58174 | | |
| Peak 6 | 5.637 | 238610 | 12895 | | |
| Peak 7 | 6.991 | 701082 | 52840 | | |
| Peak 8 | 9.116 | 8294229 | 664171 | | |
| Peak 9 | 10.787 | 1828968 | 101867 | | |
| Peak 10 | 10.417 | 202222 | 17165 | | |
| Peak 11 | 10.787 | 1051607 | 58427 | | |
| Peak 12 | 12.086 | 1023319 | 85427 | | |
| Peak 13 | 13.681 | 1497954 | 135388 | | |
| Peak 14 | 14.015 | 4682829 | 433278 | | |
| Peak 15 | 14.723 | 284010 | 26563 | | |
| Peak 16 | 16.497 | 477570 | 18585 | | |
| Peak 17 | 17.082 | 300708 | 21528 | | |
| Peak 18 | 18.796 | 398406 | 32457 | | |
| Peak 19 | 19.206 | 707129 | 58308 | | |
| Peak 20 | 20.092 | 920167 | 58499 | | |
| Peak 21 | 21.019 | 286029 | 29773 | | |
| Peak 22 | 22.695 | 527555 | 49406 | | |
| Peak 23 | 27.790 | 1054908 | 23858 | | |

2) Fingerprint Chromatogram of the Radix Scutellariae Extract a) Apparatus and Material
i) Instrument: Waters 510 HPLC Pump (American), Waters TM 996 PDA Photodiode Array Detector Waters pump Control Module. Chromatography Working Station: Millenium 32, Pentum III, UV wave. Swirlly mixer: XW-80A, Centrifugal precipitator: 80–1.
ii) Regent: Acetonitrile (HPLC) purchased by Shanghai Xingshi Biological Engineering Co. LTD; Methol (HPLC) purchased by Shanghai chemical regent Co., Glacial acetic acid and Sparklin pure distilled water.
iii) Standard Sample: Baicalin purchased from the Drug and Biological Product Testing Agency of China.

b) Preparation of the Sample Solution
Take the extractor of Radix scutellariae and rub it into powder, and pass the 40 item of bolt. Weigh exactly 20 mg of the powder, put it into the centrifuge tube and add 4 ml of methanol/water into a mixer and mix them for 1 min, then ultrasonically vibrate the solution for 15 min. Centrifuge it and take the upper clear solution. Add 4 ml of methanol/water into the residue and vibrate it under ultrasonic waves for another 15 min. Centrifuge the solution and take the upper clear solution. Wash the residue with 1.5 ml of methanol/water and combine it with the upper clear solution, and scale the sample solution in a 10 ml of flask. Filter the solution with 0.45 um of filtration membrane before giving sample.

c) Fingerprint Chromatogram of the Extracts of Radix Scutellariae

Take the above sample solution under the Chromatographic Condition to have HPLC analysis. The result is given in Table 23. The number of peak is 4 at low limit and 5 at high limit. The peak area of the HPLC-FPS is about $2.0 \times 10^6$ and over. The $1^{st}$ peak of the HPLC-FPS is known as the characteristic peak of Baicalin, the $5^{th}$ peak of the HPLC-FPS is known as the characteristic peak of Baicalein. The conditions of characteristic peak of Baicalin and Baicalein were limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 6.

TABLE 23

Peak Results of the Extracts of Radix Scutellariae

| Peak No. | RT | Area | Height | Amount | Units |
|---|---|---|---|---|---|
| Peak 1 | 22.607 | 18749381 | 1496061 | | |
| Peak 2 | 25.072 | 2486083 | 198168 | | |
| Peak 3 | 26.417 | 10114109 | 766644 | | |
| Peak 4 | 27.509 | 1765044 | 21991 | | |
| Peak 5 | 29.556 | 442502 | 35154 | | |

3. Quality Standard of the Drug Product Preparation

A. Content Determination

1) Content Determination of Chlorogenic Acid of the Drug Product a) Apparatus and Material i) Apparatus:

Chromatographic Working Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory.

ii) Sample:

New drug product with the coating film (batch number is 00912).

b) Chromatographic Condition

Chromatographic Column: Inertsil ODS-3,5 μm, 4.6*250 mm (Made in Japan). Protecting Column: Phenomenex C18 (ODS), 4 mml*3.0 mmID. Floating Phase: methanol: water (contain 2% acetic acid)=25:75 Velocity of flow: 1 ml/min. Testing Wavelength: 280 nm, column temperature: room temperature.

c) Standard Curve

Preparation of Standard Solution: Weighing exactly a certain amount of Chlorogenic acid dried by diphosphorus pentaoxide for 48 hr as comparing solution. Isolating it with methanol/water (1:1) (V/V), preparing it into 0.5 mg/ml of concentration.

Take the standard solution and inject the sample of 2.5, 5, 10, 15 and 20 ul under the Chromatographic Condition. Record the sample volume and the peak areas. Calculate the following regression equation:

$A=450580+3941609.92C$; $r=0.9992$; Linear Range: 1.25 ug–10 ug.

d) Preparation of the Sample

Preparation of the Sample Solution:

Take the drug product with new technique and rub the drug product into powder after removing the coating, then pass the 40 item of bolt. Weigh exactly 0.5 g of the powder and put it to a centrifuge tube. Add 4 ml of methanol/water into a mixer and mixing them for 1 min. Then vibrate the solution under ultrasonic waves and extract it for 15 min. Centrifuge it and take the upper clear solution. Wash the residue with 1.5 ml of methanol/water, combine it with the upper clear, and scale the sample solution in a 10 ml of flask. Filter the solution with 0.45 um of filtration membrane before giving sample.

Take the sample solution under the above-mentioned chromatographic condition to perform HPLC analysis. Calculate the ingredient content of the sample according to the two-point revise method. The formula is given as follows:

$$Cx=C1+(C2-C1)*(Ax-A1)/(A2-A1)$$

C1 and C2 stand for the qualities of the standard sample respectively.

A1 and A2 stand for the peak areas of the standard sample respectively.

Cx and Ax stand for the quality and the peak area of the sample.

e) Examples of Content Determination

Example 1

Take the drug product of Flos Lonicerae, Fructus Forsythiae and Radix Scutellariae and determine the content of Chlorogenic acid according to the above-mentioned term. The content of Chlorogenic acid is about 1.64%.

Example 2

Take the drug product of Flos Lonicerae, Fructus Forsythiae and Radix Scutellariae and determine the content of Chlorogenic acid according to the above-mentioned term. The content of Chlorogenic acid is about 1.05%.

Example 3

Take the drug product of Flos Lonicerae, Fructus Forsythiae and Radix Scutellariae and determine the content of Chlorogenic acid according to the term above mentioned. The content of Chlorogenic acid is about 1.28%.

Result: 1.05%–1.68%.

2) Content Determination of Phillyrin of the Drug Product a) Apparatus and Material i) Apparatus:

Chromatographic Working Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory ii) Sample:

New drug product with the coating film (batch number is 00912).

b) Chromatographic Condition

Chromatographic Column: Inerysil ODS-3,5 μm, 4.6*250 mm (Made in Japan). Protecting Column: Phenomenex C18 (ODS), 4 mm*3.0 mmID. Floating Phase: acetonitrile: water=28:72.

Velocity of flow: 1 ml/min. Testing Wavelength: 280 nm. Column temperature: room temperature.

c) Standard Curve

Preparation of Stabndard solution:

Weigh exactly a certain amount of Phillyrin dried with $P_2O_5$ for 48 hrs to be used as comparing solution. Isolate it with methanol/water (1:1 v/v) and prepare with it a solution with 0.5 mg/ml of concentration.

Take the standard solution under the above chromatographic condition. Inject a sample solution of 2.5 ul, 5 ul, 10 ul, and 20 ul respectively and record the peak areas and the sample volume. Calculate the regression equation:

$$A=51826+1897520.24C,\ r=0.9998,\ \text{Linear range: 1.25 ug–10 ug}.$$

d) Determination of the Sample

Preparation of the Sample solution:

Take the drug product of Flos Lonicerae, Fructus Forsythiae and Radix Scutellariae and rub it into powder after removing the coatin and pass it into 40 item of bolt. Weigh exactly 0.5 g of the powder and put it into the centrifuge tube. Add the solution of methanol/water 4 ml into a mixer and mix them for 1 min. Vibrate it under ultrasonic waves and extract the solution for 15 min. Centrifuge it and take the upper clear solution. Add methanol/water 1.5 ml to the residue and vibrate under ultrasonic waves for another 15 min. Centrifuge it and take the upper clear solution. Wash the residue with methanol/water 1.5 ml and combine the cleaning solution with the upper clear solution. Scale the sample solution in a 10 ml of flask. Filter it with 0.45 um filtration before giving sample.

Take the above sample solution under the above-mentioned Chromatographic Condition to have HPLC analysis. Calculate the ingredient content of the sample according to the two-point revise method. The formula is given as follows:

$$Cx=C1+(C2-C1)*(Ax-A1)/(A2-A1)$$

C1 and C2 stand for the qualities of the standard sample respectively.

A1 and A2 stand for the peak areas of the standard sample respectively.

Cx and Ax stand for the quality and the peak area of the sample.

e) Examples of Content Determination

Example 1

Take the drug product of Flos Lonicerae, Fructus Forsythiae and Radix Scutellariae to be determined according to the above-mentioned term. The content of Phillyrin is about 0.52%.

Example 2

Take the drug product of Flos Lonicerae, Fructus Forsythiae and Radix Scutellariae to be determined according to the above-mentioned term. The content of Phillyrin is about 0.61%.

Example 3

Take the drug product of Flos Lonicerae, Fructus Forsythiae and Radix Scutellariae to be determined according to the above-mentioned term. The content of Phillyrin is about 0.70%.

Result: 0.10%–0.40%.

3) Content Determination of Baicalin of the Drug Product a) Apparatus and Material i) Apparatus:

Chromatographic Working Station: Perkin ELMER 1022 LC Plus. Pump: Perkin ELMER series 200 LC pump. Detector: PERKIN ELMER DAD 235C. Volution mixer: Shanghai Medical University Apparatus Factory. Centrifuge and deposition machine: Shanghai operation instruments factory. Bath boiler: Jangsu Changhsu Medical Instrument Factory.

ii) Sample:

New drug product with the coating film (Batch number is 00912).

b) Chromatographic Condition

Chromatographic Column: Inerysil ODS-3,5 $\mu$m, 4.6*250 mm (mada in Japan). Protecting Column: phenomenex C18 (ODS), 4 mml*3.0 mmID. Floating Phase: methanol: water (contain 2% acetic acid)=65:35. Velocity of flow: 1 ml/min. Testing Wavelength: 280 nm. Column temperature: room temperature.

c) Standard Curve

Preparation of Standard Solution:

Weigh exactly a certain amount of Baicatin previously dried with $P_2O_5$ for 48 hrs in order to be used as the comparing solution. Isolate it with methanol/water (1:1 v/v). Prepare the solution with 0.1 mg/ml of concentration.

Put the standard solution under chromatographic conditions and inject a sample of 2.5 ul, 5 ul, 10 ul, and 20 ul, respectively. Record the peak areas and the sample volume, and calculate the regression equation:

$$A=-308002+14174938.4C;\ r=0.9993;\ \text{Linear range: 0.25 ug–2 ug}.$$

d) Determination of the Sample

Preparation of the Sample Solution:

Take the drug product of Flos Lonicerae, Fructus Forsythiae and Radix Scutellariae and rub it into powder after removing the coating, and then pass the 40 item of bolt. Weigh exactly 0.1 g of the powder and put it into a 50 ml of bottle. Add methanol/water into a mixer and mix them for 1 min. Then vibrate under ultrasonic waves and extract it for 15 min. Scale the sample solution in a 10 ml of flask. Filter it with 0.45 um filtration before giving sample.

Take the sample solution under the above-mentioned Chromatographic Condition to have the HPLC analysis. Calculate the ingredient content of the sample according to the two-point revise method. The formula is given as follows:

$$Cx=C1+(C2-C1)*(Ax-A1)/(A2-A1)$$

C1 and C2 stand for the qualities of the standard sample respectively.

A1 and A2 stand for the peak areas of the standard sample respectively.

Cx and Ax stand for the quality and the peak area of the sample.

e) Examples of Content Determination

Example 1

Take the drug product of Flos Lonicerae, Fructus Forsythiae and Radix Scutellariae to be determined according to the above-mentioned term. The content of Baicalin is about 9.04%.

Example 2

Take the drug product of Flos Lonicerae, Fructus Forsythiae and Radix Scutellariae to be determined according to the above-mentioned term. The content of Baicalin is about 9.07%.

Example 3

Take the drug product of Flos Lonicerae, Fructus Forsythiae and Radix Scutellariae to be determined according to the above-mentioned term. The content of Baicalin is about 8.71%.

Result: 8.71%–14.80%

4) Qualitative Control of Supercritical Fluid Extraction a) Material

The extracts of Flos Lonicerae and Fructus Forsythiae were extracted with the $CO_2$ Supercritical Fluid Extraction.

b) Apparatus

GC-9A Gas Chromatograph Chromatopac C-E1B data processing instrument (made in Japan)

c) Test Method

Gas Chromatographic Condition:

Use a SE-54 elastic quart chromatographic column with a 30-meter length and a 0.32 mm inner diameter. The temperature of gasification room is about 250° C. The column temperature ranges from 50–230° C., rising 4° C./min controlled by procedure. The carried gas is Nitrogen with pre-column pressure of 0.7 kg/cm. The column volume is 2 ml/min. The volume of injection if 0.4 ul. The detector is FID.

d) Qualitative control

Example 1

Use the Gas Chromatography and contrast the sample with the standard solution. When the value of TR is about $tR1=8.476$ min, β-pinene can be got. When the value of TR is about $tR2=12.925$ min, linalool can be got.

Example 2

Use the Gas Chromatography and contrast the sample with the standard solution. When the value if TR is about 8.513 min, β-pinene can be got. When the value of TR is about 12.945 min, linalool can be got.

Example 3

Use the Gas Chromatography and contrast the sample with the standard solution. When the value of TR is about 8.524 min, β-pinene can be got. When the value of TR is about 12.828 min, linalool can be got.

C. Fingerprint Chromatogram of the drug product

1) Apparatus

Waters 510 HPLC Pump (American), Waters TM 996 PDA Photodiode Array Detector Waters pump Control Module. Chromatography Working Station: Millenium 32, Pentum III, UV wave. Swirlly mixer: XW-80A. Centrifugal precipitator: 80–1.

2) Materia a) Regent: Acetonitrile (HPLC) purchased by Shanghai Xingshi Biological Engineering Co., LTD. Methol (HPLC) purchased by Shanghai chemical regent Co. Glacial acetic acid and Sparklin pure distilled water.

b) Standard Sample: Chlorogenic acid, Phillyrin and Baicalin that are purchased from Institute of Drug and Biological Product Testing of China.

c) Sample: New drug product with coating film (Batch number is 00912).

d) Reference: refer to published references of the HPLC-FPS of Caffeic acid and Baicalein.

2) Chromatographic Condition

Chromatographic column: as the above mentioned: Inertsil ODS-3,5 μm, 4.6 mm*250 mm (made in Japan). Protecting Column: phenomenex C18 (ODS), 4 mml*3.0 mmID. Floating Phase: acetonitrile: 1% acetic acid (V/V). Temperature: room temperature (air-condition in room is between 18~22° C.). Testing machine: Inspector PDA, whole wavelength scan of 210~400 nm.

3) Preparation of the Sample Solution

Take the drug product of Flos Lonicerae, Fructus Forsythiae and Radix Scutellariae and rub it into powder after removing the coating, then pass of the 40-item bolt. Weigh up exactly 200 mg of the powder and put it into the centrifuge tube. Add 4 ml of methanol/water into a mixer and mix it for 1 min. Then ultrasonically vibrate and extract the solution for 15 min. Centrifuge it and take the upper clear solution. Add 4 ml of methanol/water to the residue and ultrasonically vibrate it for another 15 min. Centrifuge it and take the upper solution. Wash the residue with 1.5 ml of methanol/water and combine it with the upper clear solution. Scale the sample solution in a 10 ml of flask. Filter the solution with 0.45 um filtration before giving sample.

4) Fingerprint Chromatogram of the drug product (HPLC-FPS)

Take the above sample solution and have HPLC analysis under the above-mentioned Chromatographic Condition. The result is given in Table 24. The number of peak is about 27 at low limit and 30 at high limit, when the peak area of the HPLC-FPS is over $1.95 \times 10^6$. In the HPLC-FPS Peak Results, the $4^{th}$ of peak was known as the charateristic peak of Chlorogenic acid. The $5^{th}$ peak was known as the charateristic peak of Caffeic acid. The $21^{st}$ peak was known as the charateristic peak of Phillyrin. The $22^{nd}$ and the $30^{th}$ peaks were respectively known as the charateristic peaks of Baicalin and Baicalein. The conditions of characteristic peaks of Chlorogenic acid, Caffeic acid, Phillyrin, Baicalin and Baicalein were limited under the following: Inertsil ODS-3,5 μm, 4.6 mm*250 mm of chromatographic Column, 210–400 nm of testing wavelength and 18–22° C. of room temperature. The sample information refers to the Auto-Scaled Chromatogram given in FIG. 7.

TABLE 24

HPLC-FPS of the drug product

| Peak No. | RT | Area | Height | Amount | Units |
|---|---|---|---|---|---|
| Peak 1 | 4.452 | 205592 | 38707 | | |
| Peak 2 | 6.224 | 299812 | 21033 | | |
| Peak 3 | 7.120 | 197099 | 11059 | | |
| Peak 4 | 8.969 | 859033 | 80929 | | |
| Peak 5 | 12.893 | 289803 | 13870 | | |
| Peak 6 | 13.469 | 388059 | 33424 | | |
| Peak 7 | 13.664 | 1081332 | 89657 | | |
| Peak 8 | 14.455 | 249863 | 11072 | | |
| Peak 9 | 14.935 | 229019 | 10680 | | |
| Peak 10 | 15.381 | 371728 | 18089 | | |
| Peak 11 | 15.702 | 361194 | 19883 | | |
| Peak 12 | 16.396 | 530822 | 29253 | | |
| Peak 13 | 16.962 | 322271 | 14947 | | |
| Peak 14 | 17.239 | 822033 | 50090 | | |
| Peak 15 | 17.846 | 469827 | 18948 | | |
| Peak 16 | 18.359 | 305826 | 19057 | | |
| Peak 17 | 19.070 | 267976 | 14063 | | |
| Peak 18 | 19.360 | 572454 | 34344 | | |
| Peak 19 | 19.826 | 213452 | 11461 | | |
| Peak 20 | 20.448 | 830745 | 38803 | | |
| Peak 21 | 21.207 | 384227 | 22545 | | |
| Peak 22 | 22.062 | 47506934 | 3066456 | | |
| Peak 23 | 22.941 | 291756 | 15251 | | |
| Peak 24 | 23.383 | 218783 | 12559 | | |
| Peak 25 | 23.804 | 240257 | 11245 | | |
| Peak 26 | 24.784 | 2353400 | 167244 | | |
| Peak 27 | 25.128 | 733507 | 65959 | | |
| Peak 28 | 26.174 | 2952888 | 262798 | | |

TABLE 24-continued

HPLC-FPS of the drug product

| Peak No. | RT | Area | Height | Amount | Units |
|---|---|---|---|---|---|
| Peak 29 | 26.800 | 229318 | 20662 | | |
| Peak 30 | 29.537 | 722352 | 60740 | | |

What is claimed is:

1. A composition comprising a supercritical extract of Flos Lonicerae and Fructus Forsythiae, an aqueous extract of Flos Lonicerae and Fructus Forsythiae, aqueous extract of and Radix Scutellariae, and a suitable carrier.

2. An antiviral, antibacterial, anti-anaphylaxis, anti-inflammatory or antifebrile pharmaceutical composition comprising the composition of claim 1.

3. A composition of claim 1, wherein the ratio of ingredients for Flos Lonicerae, Fructus Forsythiae and Radix Scutellariae is approximately 1:2:1.

4. A composition of claim 1, comprising about 90–180 parts of aqueous extract of Flos Lonicerae and Fructus Forsythiae about, 10–60 parts of supercritical carbon dioxide ($CO_2$) extract of Floe Lonicerae and Fructus Forsythiae, about 30–50 parts of aqueous extract of Radix Scutellariae and 23–125 parts of a suitable carrier.

5. A composition of claim 4 comprising about 0.01 percent to about 99.99 percent of effective combination of extracts, and about 99.99 percent to 0.01 percent of a suitable carrier.

6. A composition of claim 4 wherein said combination of extracts are present in the following formula: about 10 percent to 100 percent Floe Lonicerae, about 10 percent to 100 percent Fructus Forsythiae and about 10 percent to 100 percent Radix Scutellariae.

7. A composition as in claim 4 further comprising about 1.3 percent to 1.6 percent of chlorogenic acid, 0.2 percent to 0.3 percent of phillyrin and about 14.1 percent to 15.3 percent of baicalin.

8. The composition of claim 2, wherein said combination et extracts has antiviral activity against Herpes I virus and Herpes II virus.

9. An antibacterial composition of claim 2, wherein said combination of extracts has antibacterial activity against *Bacillus cereus, Shigella shigae* and *Escherichia coli*.

10. An anti-anaphylaxis composition of claim 2, wherein said combination of extracts inhibits ileum contraction induced by histamine.

11. An anti-inflammatory composition of claim 2, wherein said combination of extracts inhibits leukotaxis, xylene-induced inflammation and albumen-induced inflammation.

12. An antifebrile composition of claim 2, wherein said combination of extracts can inhibits typhoparatyphoid A anal B-induced pyrexy.

* * * * *